(12) United States Patent
Dwyer et al.

(10) Patent No.: US 8,821,621 B2
(45) Date of Patent: Sep. 2, 2014

(54) FILTER SYSTEMS INCLUDING OPTICAL ANALYTE SENSORS AND OPTICAL READERS

(75) Inventors: Gary E. Dwyer, Mallorytown (CA); Thomas W. Holmquist-Brown, Hastings, MN (US); Kiran S. Kanukurthy, Cottage Grove, MN (US); Neal A. Rakow, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 162 days.

(21) Appl. No.: 13/634,154

(22) PCT Filed: Mar. 29, 2011

(86) PCT No.: PCT/US2011/030237
§ 371 (c)(1),
(2), (4) Date: Sep. 11, 2012

(87) PCT Pub. No.: WO2011/123403
PCT Pub. Date: Oct. 6, 2011

(65) Prior Publication Data
US 2013/0010288 A1 Jan. 10, 2013

Related U.S. Application Data

(60) Provisional application No. 61/320,427, filed on Apr. 2, 2010.

(51) Int. Cl.
| | | |
|---|---|---|
| *A62B 7/00* | (2006.01) | |
| *A62B 9/04* | (2006.01) | |
| *A62B 18/08* | (2006.01) | |
| *A62B 23/02* | (2006.01) | |
| *G01N 21/78* | (2006.01) | |
| *G01N 21/31* | (2006.01) | |
| *G01N 21/77* | (2006.01) | |

(52) U.S. Cl.
CPC ............. *G01N 21/783* (2013.01); *A62B 23/02* (2013.01); *G01N 2021/3148* (2013.01); *A62B 18/088* (2013.01); *G01N 2021/7723* (2013.01); *Y10S 55/34* (2013.01); *Y10S 55/35* (2013.01); *Y10S 55/33* (2013.01)
USPC ............ 96/416; 96/417; 96/418; 55/DIG. 34; 55/DIG. 35; 55/DIG. 33; 128/202.22; 128/206.21

(58) Field of Classification Search
USPC ...................... 55/385.1, DIG. 35; 96/4, 117.5; 128/202.22, 206.21; 422/119, 416, 422/68.1, 82.05, 83, 87, 88, 200.24; 429/119
See application file for complete search history.

(56) References Cited

U.S. PATENT DOCUMENTS

| | | | |
|---|---|---|---|
| 1,537,519 A | | 12/1924 | Yablick |
| 3,971,373 A | | 7/1976 | Braun |
| 4,146,887 A | | 3/1979 | Magnante |
| 4,153,661 A | * | 5/1979 | Ree et al. ........................ 264/120 |
| 4,154,586 A | * | 5/1979 | Jones et al. ................... 96/117.5 |
| 4,155,358 A | * | 5/1979 | McAllister et al. ....... 128/202.22 |
| 4,208,194 A | * | 6/1980 | Nelson ................................. 96/4 |
| 4,326,514 A | * | 4/1982 | Eian ........................ 128/202.22 |
| 4,365,627 A | | 12/1982 | Wing |
| 4,421,719 A | * | 12/1983 | Burleigh ........................ 422/416 |
| 4,530,706 A | | 7/1985 | Jones |
| 4,684,380 A | | 8/1987 | Leichnitz |
| 4,847,594 A | | 7/1989 | Stetter |
| 4,873,970 A | | 10/1989 | Freidank |
| 4,948,639 A | | 8/1990 | Brooker |
| 5,297,544 A | * | 3/1994 | May et al. ................ 128/202.22 |
| 5,323,774 A | | 6/1994 | Fehlauer |
| 5,512,882 A | | 4/1996 | Stetter |
| 5,659,296 A | | 8/1997 | Debe |
| 5,666,949 A | * | 9/1997 | Debe et al. ................ 128/202.22 |
| 5,699,188 A | | 12/1997 | Gilbert |
| 5,858,457 A | | 1/1999 | Brinker |
| 5,882,774 A | | 3/1999 | Jonza |
| 5,944,873 A | | 8/1999 | Jager |
| 6,010,751 A | | 1/2000 | Shaw |
| 6,040,777 A | | 3/2000 | Ammann |
| 6,049,419 A | | 4/2000 | Wheatley |
| 6,312,793 B1 | | 11/2001 | Grill |
| 6,375,725 B1 | | 4/2002 | Bernard |

| | | |
|---|---|---|
| 6,497,756 B1 | 12/2002 | Curado |
| 6,573,305 B1 | 6/2003 | Thunhorst |
| 7,201,036 B2 | 4/2007 | Custer |
| 7,442,237 B1 | 10/2008 | Gardner |
| 7,449,146 B2 | 11/2008 | Rakow |
| 7,503,962 B2 | 3/2009 | Attar |
| 7,556,774 B2 | 7/2009 | Rakow |
| 7,906,223 B2 | 3/2011 | Rakow |
| 8,067,110 B2 * | 11/2011 | Rakow et al. .......... 429/119 |
| 8,293,340 B2 | 10/2012 | David |
| 2004/0189982 A1 | 9/2004 | Galarneau |
| 2004/0204915 A1 | 10/2004 | Steinthal |
| 2004/0223876 A1 | 11/2004 | Kirollos |
| 2006/0096911 A1 | 5/2006 | Brey |
| 2007/0137491 A1 | 6/2007 | Attar |
| 2008/0063575 A1 * | 3/2008 | Rakow et al. .......... 422/119 |
| 2010/0277740 A1 | 11/2010 | Hulteen |
| 2011/0094514 A1 | 4/2011 | Rakow |
| 2012/0062892 A1 | 3/2012 | Wendland |
| 2012/0062893 A1 | 3/2012 | Rakow |

FOREIGN PATENT DOCUMENTS

| | | |
|---|---|---|
| CA | 2628699 | 10/2009 |
| JP | 2002-102367 | 4/2002 |
| WO | WO 95/12432 | 5/1995 |
| WO | WO 97/01778 | 1/1997 |
| WO | WO 99/27352 | 6/1999 |
| WO | WO 2005/012397 | 2/2005 |
| WO | WO 2009/029426 | 3/2009 |
| WO | WO 2011/123409 | 10/2011 |

OTHER PUBLICATIONS

Davankov, V.A., *Structure and properties of porous hypercrosslinked polystyrene sorbents 'Styrosorb'*, Pure and Applied Chemistry, vol. 61, pp. 1881-1889 (1989).
Belyakova, L.D., *Sorption of Vapors of Various Substances by Hypercrosslinked "Styrosorb" Polystyrenes*, Advances in Colloid and Interface Science, vol. 25, pp. 249-266, 1986.
Krause, B, *Bicontinuous Nanoporous Polymers by Carbon Dioxide Foaming*, Macromolecules, 2001 vol. 34, pp. 8792-8801.
Walheim, Stefan, *Nanophase-Separated Polymer Films as High-Performance Antifeflection Coatings*, Science, 1999, vol. 283, p. 520.
Ogawa, *A simple sol-gel route for the preparation of silica-surfactant mesostructured materials*, Chemical Communications, pp. 1149-1150, 1996.
Kresge, C.T., *Ordered mesoporous molecular sieves synthesized by a liquid-crystal template*, mechanism, Letters to Nature, vol. 359, pp. 710-712, 1999.
Jia, Jianguang, *Synthesis of Microporous Silica Templated by Gelatin*, Chemistry Letters, vol. 33(2), pp. 202-203, 2004.
Wei, *A Non-surfactant Templating Route to Mesoporous Silica Materials*, Advanced Materials, 1998, vol. 10, p. 313-316, 1998.
Budd, *Polymers of intrinsic microporosity (PIMs): robust, solution-processable, organic nanoporous materials*, ChemComm, 2004, pp. 230-231.
Budd, *Free volume and intrinsic microporosity in polymers*, Journal of Materials Chemistry, 2004, 15, pp. 1977-1986.
McKeown, *Polymers of Intrinsic Microporosity*, Chemistry A European Journal, 2005, 11, pp. 2610-2620.
Favas, G., End of service life indicator (ESLI) for respirator cartridges. Part I: Literature review, DSTO-TN-0657, Commonwealth of Australia, Jul. 2005, pp. 1-39.
International Search Report, PCT/US/2011/030237, mailed May 17, 2011, 4 pages.

* cited by examiner

*Primary Examiner* — Duane Smith
*Assistant Examiner* — Minh-Chau Pham
(74) *Attorney, Agent, or Firm* — Kenneth B. Wood

(57) ABSTRACT

A filter system includes a housing, a filter medium disposed within the housing and a optical analyte sensor also disposed within the housing in fluid communication with the filter medium. The optical analyte sensor includes a detection medium that changes at least one of its optical characteristics in response to an analyte. The filter system further includes an optical reader having at least one light source and at least one detector. The optical reader is attached to the housing such that at least a portion of light emitted by at least one light source is reflected from the optical analyte sensor and captured by at least one detector.

11 Claims, 17 Drawing Sheets

FILTER SYSTEMS INCLUDING OPTICAL ANALYTE SENSORS AND OPTICAL READERS

CROSS REFERENCE TO RELATED APPLICATIONS

This application is a national stage filing under 35 U.S.C. 371 of PCT/US2011/030237, filed Mar. 29, 2011, which claims priority to U.S. Provisional Application No. 61/320,427, filed Apr. 2, 2010, the disclosure of which is incorporated by reference in its/their entirety herein.

FIELD OF THE INVENTION

The present disclosure relates to filter systems that include a filter medium, an optical analyte sensor disposed in fluid communication with the filter medium, and an optical reader configured and disposed to interrogate the optical analyte sensor.

BACKGROUND

Filter systems are commonly used in the presence of vapors and other hazardous airborne substances. Exemplary filter systems include collective protection systems, disposable personal respirators, reusable personal respirators, powered air purifying respirators, haz-mat suits and other protective devices.

Various chemical, optical or electronic indicators have been proposed for warning users of protective devices of the presence of undesired materials. For example, an end-of-service-life indicator ("ESLI") can warn that a filter element in such a device may be approaching saturation or may be ineffective against a particular material.

The ability to detect chemical analytes, especially organic chemical analytes, is important in many applications, including environmental monitoring and the like. Some devices that have been used for detection of chemical analytes have been developed, for example optical, gravimetric, microelectronic, mechanical, and colorimetric.

SUMMARY

The present disclosure is directed to a filter system that includes a housing and a filter medium disposed within the housing. The filter system further includes an optical analyte sensor disposed within the housing such that the detection medium is in fluid communication with the filter medium. The optical analyte sensor includes a detection medium that changes at least one of its optical characteristics in response to an analyte. The filter system also includes an optical reader comprising at least one light source and at least one detector. The optical reader is attached to the housing, such that at least a portion of light emitted by at least one light source is reflected from the optical analyte sensor and captured by at least one detector. In some exemplary embodiments, the optical reader is permanently or removably attached to the housing. In some exemplary embodiments, the optical reader may be permanently or removably attached to a removable housing portion.

BRIEF DESCRIPTION OF THE DRAWINGS

The disclosure may be more completely understood in consideration of the following detailed description of various embodiments in connection with the accompanying drawings, wherein.

Figure 1:
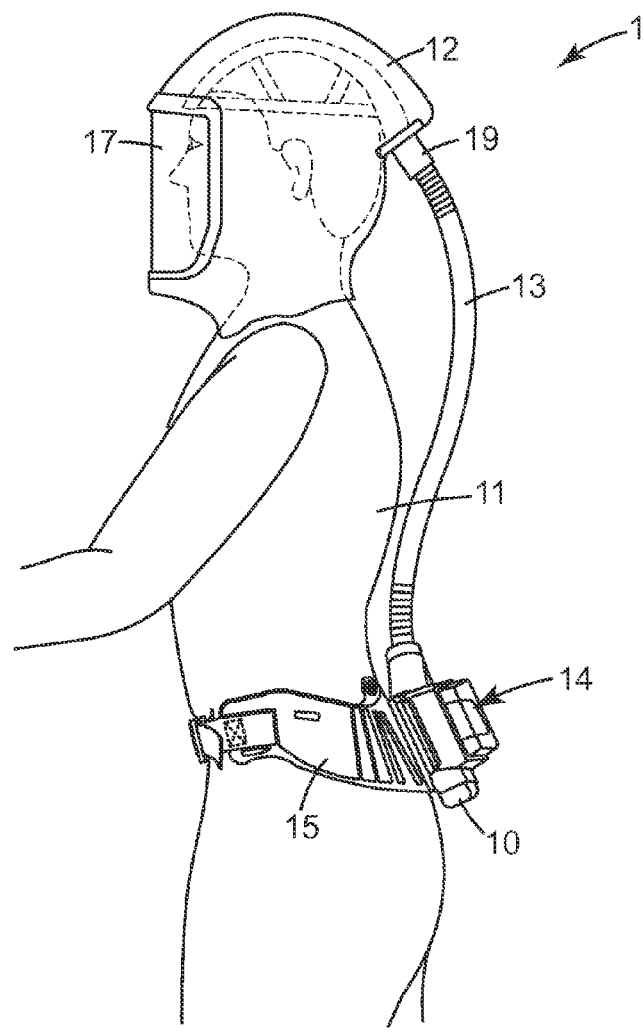
FIG. 1 shows one exemplary filter system according to the present disclosure.

Like reference symbols in the various figures indicate like elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", lower", "under", "over", "front", "back", "outward", "inward", "up" and "down", and "first" and "second" may be used in this disclosure, it should be understood that those terms are used in their relative sense only unless otherwise noted.

DETAILED DESCRIPTION

In the following description, reference is made to the accompanying drawings that form a part hereof, and in which are shown by way of illustration several specific embodiments. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure is directed to systems and devices that may be applied to indicate an end of service life or provide a user with information related to an end of service life of a filter medium, such as that of a respiratory filter or cartridge used in hazardous environments for protection against volatile organic compounds. It is expected that the present disclosure will help provide a more accurate end of service life indication for various filter systems. It is envisioned that some exemplary embodiments may be provided as accessories for respirator cartridges and filters, while other exemplary embodiments include entire respirators and cartridges. The present disclosure is applicable to various filter systems, such as personal respirators, including powered air purifying respirators, reusable personal respirators, disposable personal respirators, hazmat suits, collective protection filters and other applications that will be familiar to those skilled in the art.

Exemplary embodiments of the present disclosure may be used to detect and/or monitor one or more analytes of interest. Such an analyte may comprise a vapor or gas that may be present in an environment (often, an air atmosphere) that is desired to be monitored. In some embodiments, the analyte is an organic vapor (e.g., a volatile organic compound). Representative organic analytes may include, without limitation, substituted or unsubstituted carbon compounds including alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, toluene, styrene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, acetonitrile, and the like. Although organic vapor sensors are mentioned as one particular type of optical analyte sensors according to the present disclosure, other types of optical analyte sensors that may be employed include those that respond to organic vapors, reactive gases, such as acidic (for example, $SO_2$, $Cl_2$, HCl, ClO2, HCN, HF, $H_2S$ and oxides of nitrogen) and basic gases (for example, ammonia, methylamine), and other gases such as cyanogen chloride and formaldehyde.

An exemplary filter system according to the present disclosure is illustrated in FIG. 1, which shows schematically a powered air purifying respirator (PAPR) 1. The PAPR 1 includes a head top, such as a hood 12, a turbo unit 14, a breathing tube 13 and a belt 15. The hood 12 is configured to be worn over the head of a user 11 and to at least partially enclose the user's head to form a breathing zone 17, that is, the area around the user's nose and mouth, so that the filtered air is directed to this breathing zone 17. Although a hood is illustrated in FIG. 1, the hood 12 could be substituted by any other suitable head top, such as a mask, a helmet or a full suit, provided that a closed user environment, covering at least the orinasal area of the user's face, to direct air to the user's breathing zone 17, is created. The turbo unit 14 may be attached to a belt 15 to enable it to be secured about the user's torso.

The turbo unit 14 houses a blower system (not shown), which draws the air through the PAPR system using a fan powered by a motor (also not shown). The turbo unit can further include a power source, such as a battery pack 10. The turbo unit 14 supplies air to the hood 12 through the breathing tube 13, which is connected between the outlet 18 of the turbo unit 14 and the inlet 19 of the hood 12. The turbo unit 14 includes a filter cartridge (shown in FIG. 2) disposed such that the filter medium contained therein is in the airflow path, preferably disposed upstream of a fan opening of the blower. In typical embodiments of the present disclosure, the filter cartridge is removable with respect to the turbo unit and replaceable. The purpose of providing the filter cartridge is to remove at least a certain amount of contaminants, such as particles and/or gases and/or vapors from the ambient air before the air is delivered to the user 11.

Embodiments of the present disclosure may employ any one or more of a variety of filter media, one suitable category being sorbent media. The sorbent media will be capable of sorbing vapors of interest expected to be present under the intended use conditions. The sorbent media desirably are sufficiently porous to permit the ready flow of air or other gases therethrough, and may be in the form of a finely-divided solid (e.g., powder, beads, flakes, granules or agglomerates) or porous solid (e.g., an open-celled foam). Preferred sorbent media materials include activated carbon, zeolites, alumina and other metal oxides that can remove a vapor of interest by adsorption; clay and other minerals treated with acidic solutions such as acetic acid or alkaline solutions such as aqueous sodium hydroxide; molecular sieves and other zeolites; other inorganic sorbents such as silica; and organic sorbents including hypercrosslinked systems, such as the highly crosslinked styrenic polymers known as "Styrosorbs" (as described for example in V. A. Davankov and P. Tsyurupa, *Pure and Appl. Chem.*, vol. 61, pp. 1881-89 (1989) and in L. D. Belyakova, T. I. Schevchenko, V. A. Davankov and M. P. Tsyurupa, *Adv. in Colloid and Interface Sci.* vol. 25, pp. 249-66, (1986)).

Activated carbons, zeolites, and alumina are examples of preferred sorbent media. Mixtures or layers of sorbent media that can be employed, e.g., to absorb mixtures of vapors or other analytes of interest. If in a finely divided form, the sorbent particle size can vary a great deal and usually will be chosen based in part on the intended service conditions. As a general guide, finely-divided sorbent media particles may vary in size from about 4 to about 3000 micrometers average diameter, e.g., from about 30 to about 1500 micrometers average diameter. Mixtures of sorbent media particles having different size ranges can also be employed, (e.g., in a bimodal mixture of sorbent media particles or in a multilayer arrangement employing larger sorbent particles in an upstream layer and smaller sorbent particles in a downstream layer). Sorbent media combined with a suitable binder (e.g., bonded carbon) or captured on or in a suitable support such as described in U.S. Pat No. 3,971,373 (Braun et al.), U.S. Pat. No. 4,208,194 (Nelson) and U.S. Pat. No. 4,948,639 (Brooker et al.) and in U.S. Patent Application Publication No. US 2006/0096911 A1 (Brey et al.) may also be employed.

Figure 2:
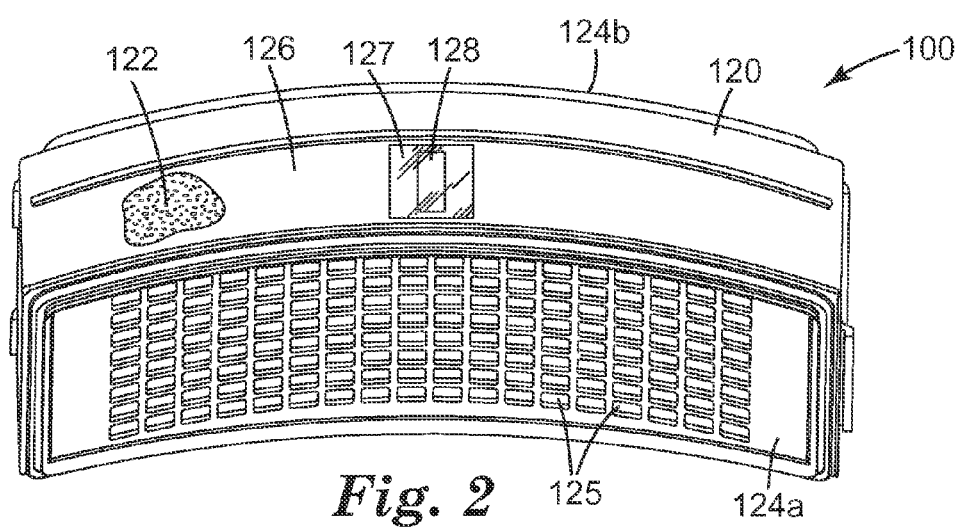
FIG. 2 shows a filter cartridge that may be used in filter systems according to the present disclosure.

FIG. 2 shows a filter cartridge 100, which may be used in turbo units of PAPRs, such as the turbo unit 14 described in connection with FIG. 1. The filter cartridge 100 includes a housing 120 and a filter medium 122, such as a sorbent material, e.g., activated carbon, disposed within the housing 120. An optical analyte sensor 128 (described in more detail below) is also disposed within the housing 120 in fluid communication with the filter medium 122, as explained in more detail below. The housing 120 illustrated in FIG. 2 includes a back cover 124a that has a plurality of openings 125 and a front cover 124b also having a plurality of openings (not shown). The openings in the front cover 124b and the back cover 124a may serve as gas inlets and outlets, respectively, permitting ambient air from the external environment to flow into cartridge 100, through the filter medium 122 and then into the fan opening of the blower of a turbo unit, of which the filter cartridge 100 is a part of. If desired, the openings in one or both of the covers 124a and 124b could be sealed until use, using, for example, a removable cover (not shown) that would be removed before use.

A wall 126 of a housing 120 may include a viewing port, such as a transparent portion 127 (which is transparent for the particular spectral range to which the light source(s) and the detector(s) are tuned), through which the optical analyte sensor 128 may be interrogated (as further explained below). If desired, a removable or replaceable shield or other covering (not shown) may optionally be used to protect the transparent portion 127 from paint or foam overspray, dust, or other obscuration. Alternatively, the viewing port may include an opening in the housing 120. In some exemplary embodiments, the entire wall 126 of the housing or the entire housing 120 may be transparent. Optical analyte sensor 128 is optically responsive to an analyte, for example, by undergoing a change in at least one of its optical properties (as may be manifested by a colorimetric change, a change in brightness, intensity of reflected light, etc.) when the filter medium 122 becomes equilibrated with the analyte at the conditions of exposure.

The light entering the transparent portion 127 and optical analyte sensor 128 is then reflected back through the transparent portion 127. The cartridge 100 would be removed and replaced with a fresh cartridge when a discernible change in at least one of the optical properties of the optical analyte sensor 128 (e.g., a change in reflectance spectrum such as from green to red, an appearance or disappearance of color such as from white or black to colored or from colored to white or black, or a change from white to black or from black to white) indicates that the filter medium 122 underneath the optical analyte sensor 128 has become equilibrated with the vapor at the conditions of exposure. In other words, the optical analyte sensor may be configured such that the optical change is indicative of the remaining service life for cartridge 100 or the end of its service life. In one embodiment, optical analyte sensor 128 could be placed at a predetermined location of the flow path so as to give warning only at the desired remaining service life percentage.

Figure 3A:
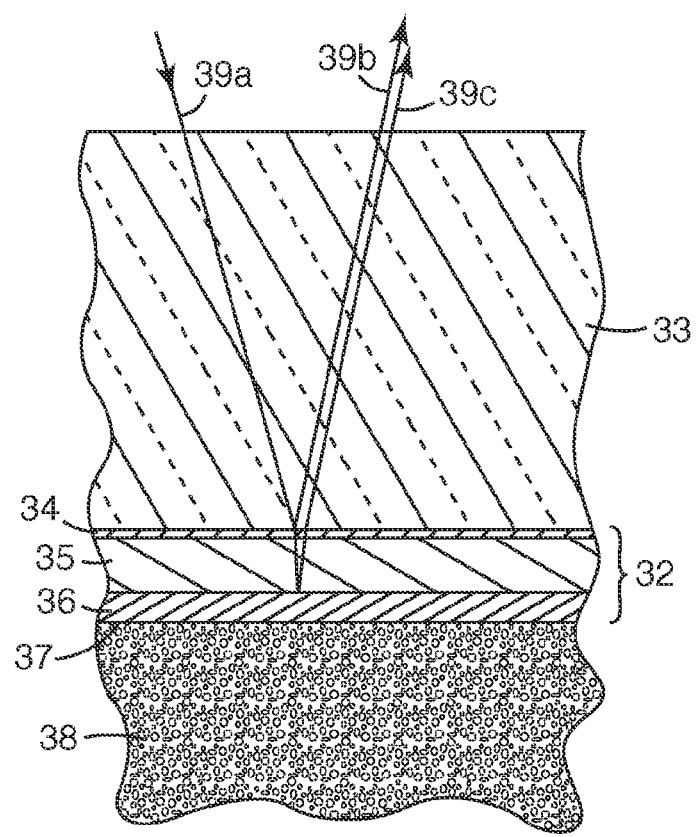
FIGS. 3A and 3B show schematically exemplary optical analyte sensors suitable for use with some exemplary embodiments of the present disclosure.

FIG. 3A shows a schematic view of an exemplary optical analyte sensor suitable for use with some exemplary embodiments of the present disclosure. A multilayer optical analyte sensor 32 is disposed between a transparent substrate 33 (which is transparent for the particular spectral range to which the light source(s) and the detector(s) are tuned) and filter medium 38. The exemplary optical analyte sensor 32 includes a partially reflective layer 34, detection medium 35 and an analyte-permeable reflective layer 36. Upon the occurrence of or soon after equilibration at the applied analyte concentration between at least a portion of the medium 38 and an analyte of interest, the analyte can pass through the analyte-permeable reflective layer 36, for example, through pores 37 into detection medium 35. Detection medium 35 can be provided in the form of a layer and it can be made from a suitable material or made with a suitable structure so that at least one of its optical characteristics (e.g., the layer's optical thickness) changes upon exposure to an analyte of interest. The change can be detected from the outside, such as through the substrate 33.

A portion of ambient light represented by ray 39a passes through substrate 33, is reflected from the partially reflective layer 34 as light ray 39b, travels back through substrate 33, and then passes outside substrate 33. Another portion of ambient light ray 39a passes through substrate 33, partially reflective layer 34 and detection medium 35 and is reflected from reflective layer 36 as light ray 39c. Light ray 39c travels back through detection layer 35, partially reflective layer 34 and substrate 33, and then passes outside substrate 33. If an appropriate initial or changed thickness has been chosen for detection layer 35, and provided that layers 34 and 36 are sufficiently flat, then constructive or destructive interference will be created by the light rays similar to rays 39b and 39c, and a discernible change in one or more optical characteristics of optical analyte sensor 32 can be detected through the partially reflective layer 34.

The optical analyte sensors according to the present disclosure may be attached to a filter housing or other support using a variety of techniques, including film or bulk adhesives, mechanical inserts, thermal bonding, ultrasonic welding and combinations thereof. The substrate is optional, but when present it may be made from a variety of materials capable of providing a suitably transparent support for the thin-film indicator. The substrate may be rigid (e.g., glass) or flexible (e.g., a plastic film that may be handled in one or more roll processing steps). If made of a flexible material such as a suitably transparent plastic, the substrate desirably has sufficiently low vapor permeability so that the vapor(s) of interest will not be transmitted into or out of the detection medium through the partially reflective layer. If the substrate is omitted then the partially reflective layer should be sufficiently impermeable to discourage or prevent such vapor transmission. A porous substrate may if desired be placed between the permeable reflective layer and the sorbent media. For example, vapors of interest could be allowed to pass from the sorbent media through the permeable substrate and reflective layer and thence into the detection medium.

The partially reflective and reflective layers may each be made from a variety of materials that provide diffuse or preferably specular light reflection and which can cooperate when appropriately spaced apart to provide a readily visibly perceptible indicator appearance change. Suitable partially reflective and reflective layer materials include metals such as aluminum, chromium, titanium, gold, nickel, silicon, silver, palladium, platinum, titanium and alloys containing such metals; metal oxides such as chrome oxide, titanium oxide and aluminum oxide; and the multilayer optical films (including birefringent multilayer optical films) described in U.S. Pat. No. 5,699,188 (Gilbert et al.), U.S. Pat. No. 5,882,774

(Jonza et al.) and U.S. Pat. No. 6,049,419 (Wheatley et al.), and PCT Published Application No. WO 97/01778 (Ouderkirk et al.). The partially reflective and reflective layers may be the same or different. Metal nanoparticle coatings (e.g., metal nanoparticle inks) may be employed to form the reflective layer, as described in copending U.S. Patent Publication No. 2008/0063874A1 (Rakow et al.).

The partially reflective layer is less reflective than the reflective layer and transmits some incident light. The partially reflective layer may, for example, have a physical thickness of about 2 to about 50 nm, light transmission at 500 nm of about 20 to about 80%, and reflectance at 500 nm of about 80 to about 20%, or any number therebetween. The partially reflective layer may itself be impermeable to vapor (and if so desirably is continuous) and optionally coated on or otherwise adjacent to a suitable substrate. The partially reflective layer may also be permeable to vapor (and if so may, for example, be discontinuous or semicontinuous) and coated on or otherwise adjacent to a suitably vapor-impermeable substrate. The face of the partially reflective layer adjacent the detection layer desirably is flat to within about ±10 nm.

The reflective layer may, for example, have a physical thickness of about 1 to about 500 nm, light transmission at 500 nm of about 0 to about 80%, and reflectance at 500 nm of about 100 to about 20%. The reflective layer preferably is porous, patterned, discontinuous, semicontinuous or otherwise sufficiently permeable so that vapor can pass from the sorbent media through the reflective layer into the detection medium. The desired pores or discontinuities may be achieved through suitable deposition techniques or through appropriate post-deposition processing such as selective etching, reactive ion etching or patterned laser ablation. The reflective layer may also be formed by depositing a vapor-permeable metal nanoparticle layer as described in the above-mentioned U.S. Patent Publication No. 2008/0063874A1 to form a vapor-permeable layer of packed nanoparticles, with pores being provided by interstices between the nanoparticles.

The detection medium mixture may be homogeneous or heterogeneous, and may, for example, be made from a mixture of inorganic components, a mixture of organic components, or a mixture of inorganic and organic components. Detection media made from a mixture of components may provide improved detection of groups of analytes. The detection medium desirably has a range of pore sizes or a surface area selected to provide vapor sorption characteristics like those of the sorbent media. Suitable porosity can be obtained by using porous materials such as foams made from high internal phase emulsions, such as those described in U.S. Pat. No. 6,573,305 B1 (Thunhorst et al.). Porosity may also be obtained via carbon dioxide foaming to create a microporous material (see "Macromolecules", 2001, vol. 34, pp. 8792-8801), or by nanophase separation of polymer blends (see "Science", 1999, vol. 283, p. 520). In general, the pore diameters preferably are smaller than the peak wavelength of the desired indicator coloration. Nano-sized pores are preferred, e.g., with average pore sizes of about 0.5 to about 20 nm, 0.5 to about 10 nm, or 0.5 to about 5 nm.

Representative inorganic detection medium materials include porous silica, metal oxides, metal nitrides, metal oxynitrides and other inorganic materials that can be formed into transparent and porous layers of appropriate thickness for producing color or a colorimetric change by optical interference. For example, the inorganic detection medium materials may be silicon oxides, silicon nitrides, silicon oxynitrides, aluminum oxides, titanium oxides, titanium nitride, titanium oxynitride, tin oxides, zirconium oxides, zeolites or combinations thereof. Porous silica is an especially desirable inorganic detection medium material due to its robustness and compatibility with wet etching treatments.

Porous silicas may be prepared, for example, using a sol-gel processing route and made with or without an organic template. Exemplary organic templates include surfactants, e.g., anionic or nonionic surfactants such as alkyltrimethylammonium salts, poly(ethyleneoxide-co-propylene oxide) block copolymers and other surfactants or polymers that will be apparent to persons having ordinary skill in the art. The sol-gel mixture may be converted to a silicate and the organic template may be removed to leave a network of micropores within the silica. Representative porous silica materials are described in Ogawa et al., Chem. Commun. pp. 1149-1150 (1996), in Kresge et al., Nature, Vol. 359, pp. 710-712 (1992), in Jia et al., Chemistry Letters, Vol. 33(2), pp. 202-203 (2004) and in U.S. Pat. No. 5,858,457 (Brinker et al.). A variety of organic molecules may also be employed as organic templates. For example, sugars such as glucose and mannose may be used as organic templates to generate porous silicates, see Wei et al, Adv. Mater. 1998, Vol. 10, p. 313 (1998). Organo-substituted siloxanes or—organo-bis-siloxanes may be included in the sol-gel composition to render the micropores more hydrophobic and limit sorption of water vapor. Plasma chemical vapor deposition may also be employed to generate porous inorganic detection materials. This methodology generally involves forming an analyte detection layer by forming a plasma from gaseous precursors, depositing the plasma on a substrate to form an amorphous random covalent network layer, and then heating the amorphous covalent network layer to form a microporous amorphous random covalent network layer. Examples of such materials are described in U.S. Pat. No. 6,312,793 (Grill et al.) and U.S. Patent Publication No. 2007/0141580A1 (Moses et al.).

Representative organic detection medium materials include polymers, copolymers (including block copolymers) and mixtures thereof prepared or preparable from classes of monomers including hydrophobic acrylates and methacrylates, difunctional monomers, vinyl monomers, hydrocarbon monomers (olefins), silane monomers, fluorinated monomers, hydroxylated monomers, acrylamides, anhydrides, aldehyde-functionalized monomers, amine- or amine salt-functionalized monomers, acid-functionalized monomers, epoxide-functionalized monomers and mixtures or combinations thereof. The above-mentioned U.S. Patent Application Publication No. US 2004/0184948 A1 contains an extensive list of such monomers and reference is made thereto for further details. The above-mentioned polymers having intrinsic microporosity (PIMs) provide particularly desirable detection media. PIMs typically are non-network polymers that form microporous solids. Due to their typically highly rigid and contorted molecular structures, PIMs are unable to fill space efficiently, thus providing the disclosed microporous structure. Suitable PIMs include, but are not limited to, polymers disclosed in "Polymers of intrinsic microporosity (PIMs): robust, solution-processable, organic microporous materials," Budd et al., Chem. Commun., 2004, pp. 230-231. Additional PIMs are disclosed in Budd et al., J. Mater. Chem., 2005, 15, pp. 1977-1986, in McKeown et al., Chem. Eur. J. 2005, 11, No. 9, 2610-2620 and in Published PCT application No. WO 2005/012397 A2 (McKeown et al.).

One or more polymers within an organic detection medium may be at least partially crosslinked. Crosslinking may be desirable in some embodiments because it can increase mechanical stability and sensitivity to certain analytes. Crosslinking can be achieved by incorporating one or more multifunctional monomers into the detection medium, by subjecting the detection medium to, e.g., electron beam or gamma ray treatment, by adding or forming coordination compounds or ionic compounds in the detection medium, or by forming hydrogen bonds in the detection medium. In one exemplary embodiment, crosslinking is carried out in the presence of a porogen which may be subsequently extracted from the crosslinked system to yield a porous detection medium. Suitable porogens include, but are not limited to, inert organic molecules, such as normal alkanes (e.g., decane) or aromatics (e.g., benzene or toluene). Other crosslinked polymers include the above-mentioned highly crosslinked styrenic polymers.

If desired, the detection medium material may be treated to modify its surface properties or adsorption characteristics. A variety of such treatments may be employed, e.g., by exposing the micropores of an inorganic detection medium to a suitable organosilane compound. The detection medium may also or instead be treated with a suitable adhesion promoting material (e.g., a tie layer made of titanium or another suitable metal) to promote adhesion between the partially reflective or reflective layer and the detection medium. Such treatments may also be applied to the partially reflective or reflective layers to promote adhesion to the detection medium.

For many applications, the detection medium desirably is hydrophobic. This will reduce the chance that water vapor (or liquid water) will cause a change in the detection medium optical thickness and interfere with the detection of an analyte, for example, the detection of organic solvent vapors. The detection medium may be made from a single layer or from two or more sublayers. The sublayers may have a variety of configurations. For example, they may be stacked or arranged side by side. The sublayers may also be made from different materials selected to absorb different vapors of interest.

Figure 3B:
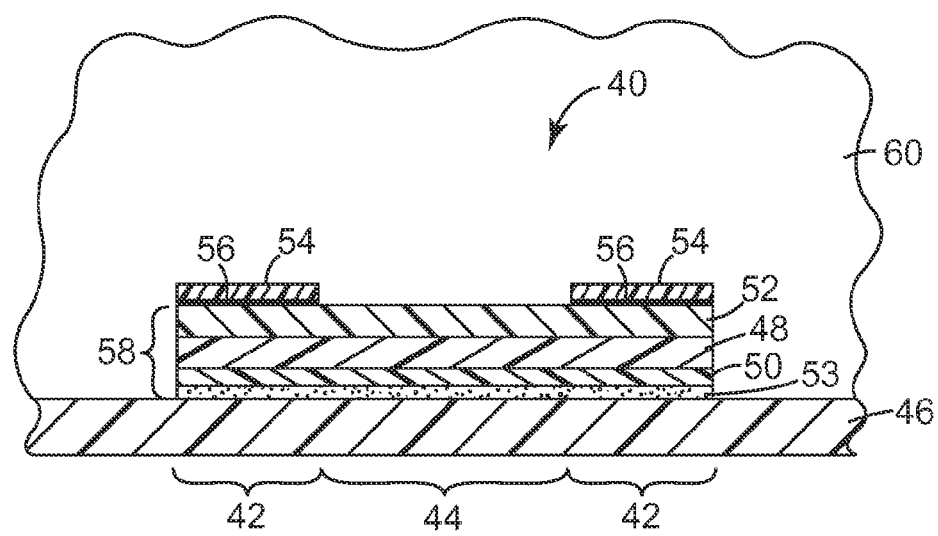

Another exemplary embodiment of an optical analyte sensor suitable for use in embodiments of the present disclosure is shown in FIG. 3B. As shown in FIG. 3B, the optical analyte sensor 40 may include one or more first regions 42 that exhibit a first response to an analyte of interest and one or more second regions 44 that exhibit a second, different, response to an analyte of interest. Such optical analyte sensors are herein referred to as patterned optical analyte sensors. In the illustrated embodiment, the optical analyte sensor 40 has a multi-layer construction, which includes a detection medium 48, a semi-reflective layer 50, and a reflective layer 52. Detection medium 48 can be provided in the form of a layer and it can be made from a suitable material or made with a suitable structure so that at least one of its optical characteristics (e.g., the layer's optical thickness) changes upon exposure to an analyte of interest. The change can be detected from the outside, such as through a substrate 46, which may comprise a wall of a housing.

The change is expected to be different in the first and second regions 42 and 44. Any detectable difference that is discerned by a detector employed is within the scope of the present disclosure. For example, in response to being exposed to an analyte of interest, different regions of an optical analyte sensor according to the present disclosure may experience different magnitudes of spectral shifts, such as different peak wavelength shifts, different intensities of reflected light, or both. Some detectors are capable detecting a difference in a color shift of as little as 1 nm. The semi-reflective layer 50 generally not permeated by the vapor. The reflective layer 52 is generally permeable to the chemical and is in fluid communication with the filter medium 60 such that the analyte of interest can pass through the reflective layer 52 into the detection medium 48 and can change at least one optical characteristic of the detection medium, such as its optical thickness, sufficiently to cause a change that can be detected by an optical reader according to the present disclosure, upon interrogation. An adhesive 53 may be used to secure the sensor 40 to an inner surface of a housing wall 46.

One way of producing an optical analyte sensor that includes one or more first regions that exhibit a first response to an analyte of interest and one or more second regions that exhibit a second, different, response to an analyte of interest, is by disposing an occluding layer 54 over a portion of a surface of the optical analyte sensor 40 that is in fluid communication with the filter medium 60. In the illustrated embodiment, occluding layers 54 are disposed on opposing sides of the second region 44, which region 44 changes color in response to exposure to one or more analytes of interest. The occluding layer 54 may be bonded to the reflective layer 52 at an interface 56 directly or via one or more intermediate layers. The interface 56 may be an adhesive layer.

Without an inert occluding layer 54 bonded to the optical analyte sensor body 58, the sensor would normally undergo a similar change in at least one of its optical characteristics over the regions 42 and 44. However, when the occluding layer 54 is disposed over the body 58, the sensor is not expected to undergo a change in at least one of its optical characteristics over the regions corresponding to the area masked by the occluding layer 54, such as the regions 42. However, the sensor is expected to undergo a change in at least one of its optical characteristics over the regions corresponding to the area not masked by the occluding layer 54, such as the regions 44. However, because in some embodiments the regions 42 and 44 may be adjacent or integral, the above-referenced change may be a progressive one. The boundary between regions 42 and 44 may be abrupt or gradual. In other exemplary embodiments, the regions may not be adjacent. The occluding layer(s) as described above may be applied to sensors to produce a variety of different visual patterns useful for interrogation according to the present disclosure.

In one embodiment, adhesives, such as pressure-sensitive adhesives may be used to form occluding layers. Polyisobutylene (PIB) adhesives are useful materials for these layers based especially on their high purity. One example of such a commercially available acrylic-based pressure sensitive adhesive transfer tape useful in embodiments of the present disclosure is 3M's adhesive transfer tape known under the trade name VLO 6690. Other pressure-sensitive adhesives useful for film body masking may include acrylic-based adhesives. In one embodiment, the pressure-sensitive adhesives may be applied to the sensor in the form of pressure-sensitive tapes, which may further include a liner and/or or backing In this implementation, the liner and/or backing often provides an additional barrier to permeation of vapors into the sensor. Hot melt, solution-free, adhesives can also be applied as masking materials. Polymeric materials can also be used as occluding layers to mask regions of the sensor, such as water-soluble polymers or epoxy materials, which may be UV or thermally curable. Waxes, resins or inorganic materials also may be used for the occluding layer.

Additionally or alternatively, any other layer or one of a set of sublayers of an exemplary optical analyte sensor may be discontinuous or patterned to achieve one or more first regions that exhibit a first response to an analyte of interest and one or more second regions that exhibit a second, different, response to an analyte of interest. Layer or sublayer patterns may also be formed by providing one or more portions that are reactive to a particular analyte and one or more portions that are non-reactive to the same analyte. A pattern of reactive material may also be deposited on a larger non-reactive sublayer, e.g., by making the patterned layer sufficiently thin so that no difference in optical thickness is apparent until an analyte is absorbed. The thickness of the detection layer may also be patterned, e.g., as described in U.S. Pat. No. 6,010,751 (Shaw et al.). This can permit a pattern to disappear (for example when a thinner portion swells to the same thickness as a thicker portion) or to appear (for example, when a portion shrinks to a lesser thickness than an adjacent portion). If desired, discontinuities may be formed in the reflective layer in the pattern of a desired shape or form. This can cause a discernible pattern to emerge or disappear upon exposure to the analyte of interest. In some cases, it may be easier to detect the contrasting optical properties of such a pattern than to detect an optical change in the overall indicator film.

The disclosed devices may include additional layers or elements if desired. For example, a porous layer of sorbent-loaded composite (e.g., a web of activated carbon particles ensconced in a matrix of fibrillated PTFE such as is described in the above-mentioned U.S. Pat. No. 4,208,194) may be placed between the reflective layer and the sorbent media, to homogenize vapors permeating into the indicator or otherwise moderate the indicator response to conditions in the sorbent media.

Various constructions and materials suitable for use in optical analyte sensors according to the present disclosure are described, for example, in U.S. Application Publication No. 2008/0063874A1 entitled "Permeable Nanoparticle Reflector," U.S. application Ser. No. 12/604,565 entitled "Patterned Chemical Sensor Having Inert Occluding Layer," and U.S. Pat. No. 7,449,146, entitled "Colorimetric Sensor." Commonly owned U.S. Application Publication No. 2008/0063575A1 and U.S. application Ser. No. 12/604,565 entitled "Patterned Chemical Sensor Having Inert Occluding Layer," describe using visibly discernible changes in the appearance of an indicator to provide a user of an organic vapor sorbent protective device with information indicative of the remaining service life or of the end of service life for a cartridge. In that application, the appearance changes in indicator could be visibly monitored under ambient lighting.

Embodiments of the present disclosure, however, include or are directed to optical readers configured to detect a change in at least one of the optical characteristics of an optical analyte sensor in response to a target analyte. The present disclosure thus is capable of providing an accurate end of service life indication without relying on a user's visual check of the color changing sensor. Visual check of the film by the user can provide an end of service life indication for some analytes, but in other cases, especially under conditions of low analyte concentration, some volatile organic compounds of interest do not produce a noticeable color change. On the other hand, some analytes produce such a massive color shift that they force the optical analyte sensor to return to its original color, which is sometimes referred to as the wrap around effect. For example, a sensor could change color from green to red to green again. Thus, some benefits of the present disclosure include increasing the range of volatile organic vapors that can be detected and preventing wrap around effects from affecting the end of service life indication.

Figure 4:
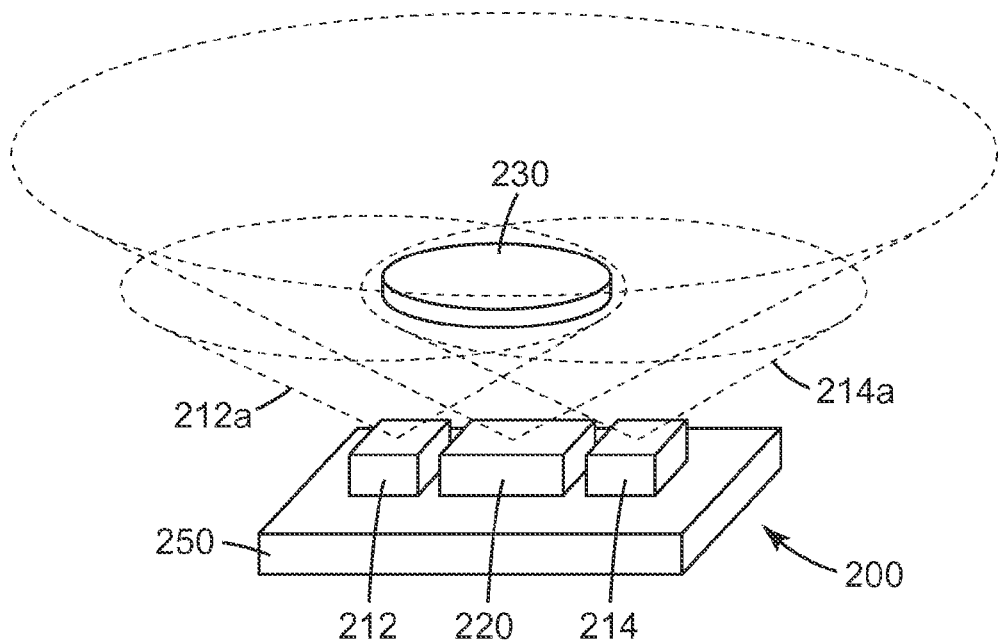
FIG. 4 shows an exemplary optical reader according to the present disclosure.

FIG. 4 shows an exemplary optical reader 200 according to the present disclosure. The optical reader 200 includes at least one light source (here, 212 and 214) and at least one detector 220. One or more light sources (e.g., 212 and 214) and one or more detectors 220 can be mounted on the same support 250. The optical reader 200 can be configured to be attached to a housing of a filter system according to the present disclosure, including an optical analyte sensor 230, such that at least a portion of light 212a, 214a emitted by at least one light source 212, 214 is reflected from the optical analyte sensor 230 and captured by the at least one detector 220.

One or more light sources (e.g., 212 and 214) may include any of a variety of light sources. For example, light-emitting diodes (LEDs) can be used. In certain embodiments, one or more light sources may include one or more relatively broadband light sources (e.g., white light sources). In other embodiments, light sources may include one or more narrowband light sources (e.g., LEDs) that emit light in a particular (e.g., relatively narrow) wavelength range with a peak at a particular wavelength within that range. In various embodiments, such narrowband light sources may be characterized by a half-power bandwidth of at most about 50 nm, at most about 40 nm, or at most about 25 nm. Exemplary LEDs that may be used include those available from Optek, Carrollton, Tex., under the designation OVLBx4C7, and surface mount LEDs such as the LS T676, LA T676, LO T676, LY T676 series from Osram.

A detector (e.g., 220) suitable for use in exemplary embodiments of the present disclosure may include any of a variety of devices capable of measuring the amount of light incident thereon, including for example photodetectors such as photomultiplier tube, a photovoltaic cell, a photodiode, a phototransistor, a charge coupled device, and the like. A suitable detector may serve to provide a signal (e.g., voltage, current, etc.) that is related to the amount of light detected (e.g., to the intensity or strength of the reflected light received from the optical analyte sensor 230) and that can be further processed as described later herein. In some embodiments one or more detectors may detect light of a particular (e.g., relatively narrow) wavelength range. In other embodiments, one or more detectors may include a broadband detector that can detect light over relatively wide range of wavelengths. In various embodiments, such broadband detectors may be able to detect light over a wavelength range of at least about 150 nm wide, 250 nm wide, or 500 nm wide. Exemplary detectors that can be used include photodiodes available from OSRAM, Regensburg, Germany, under the designation SFH 2430.

As illustrated in FIG. 4, multiple light sources may be used as a part of the optical reader 200. In the illustrated exemplary embodiment, first and second light sources 212 and 214 each may be characterized by first and second spectral (or wavelength) ranges and first and second peak wavelengths. The first spectral range may be different from the first spectral range and the first and second light sources can emit light with different peak wavelengths. In such a design, the different light sources 212 and 214 may be mounted next to a common detector 220 (an exemplary design involving a detector 220 disposed between two light sources 212 and 214 is shown in FIG. 4).

Figure 5A:
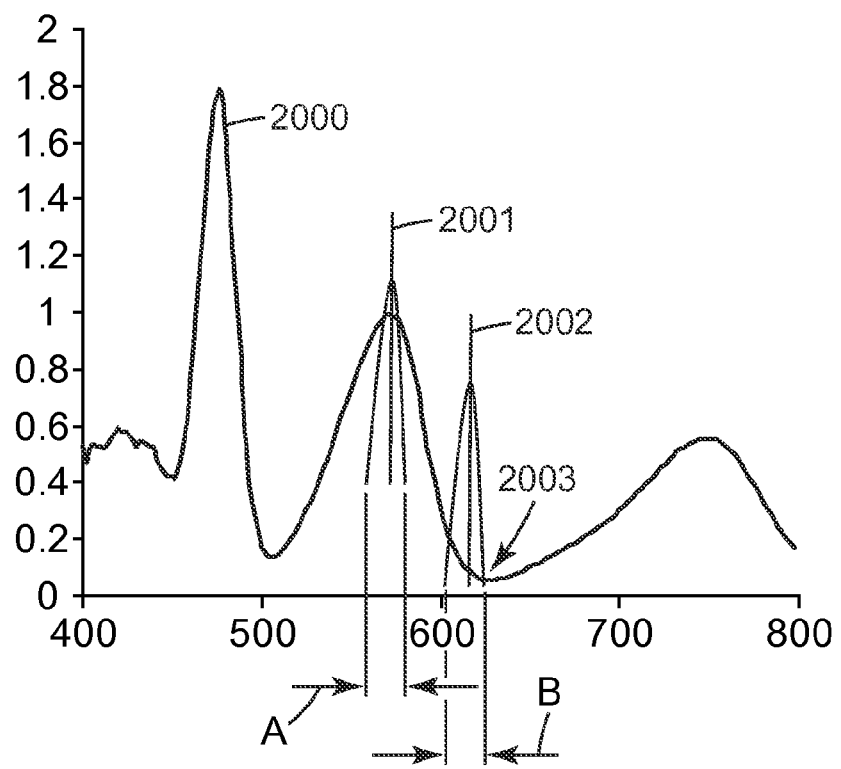
FIG. 5A shows spectra of exemplary light sources of an exemplary optical reader, as well as a spectrum of an exemplary optical analyte sensor in the absence of a target analyte.
Figure 5B:
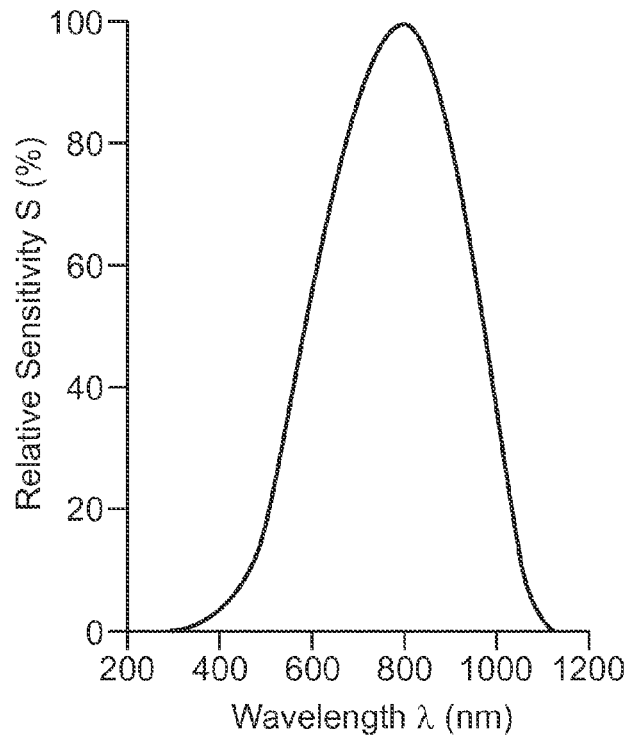
FIG. 5B shows a curve representing exemplary photodetector sensitivity to wavelength of incident light.

First and second light sources 212 and 214 may be chosen such that their spectra are characterized by different wavelength ranges A and B and different peak wavelengths corresponding to peaks 2001 and 2002 (illustrated in FIG. 5A), respectively. In such embodiments, a single (e.g., broadband) photodetector may be used as the detector 220. The monitoring of light reflected from the optical analyte sensor in multiple wavelength ranges may provide significant advantages. The various details and principles of such detection are set forth, for example, in a commonly owned U.S. Provisional Application No. 61/164,496 (Hulteen et al.). In particular embodiments, wavelength range A may be chosen to fall at or near the maximum of a peak (e.g., peak 2000 shown in FIG. 5A) in the reflection spectrum of the optical analyte sensor in the absence of a target analyte. Wavelength range B may be at least somewhat removed from wavelength range A, and in some embodiments may be at or near a valley minimum (e.g., valley minimum 2003 shown in FIG. 5A) in the reflection spectrum of an optical analyte sensor in the absence of the target analyte. In particular embodiments, wavelength B falls at or near valley minimum that is immediately adjacent to a peak of which wavelength A is monitored. FIG. 5A illustrates this concept by showing emission bands of two exemplary light sources superimposed with a reflection spectrum of an exemplary optical analyte sensor using a PIM film. Photodetector sensitivity to wavelength of incident light is shown in FIG. 5B. As the spectrum shifts towards right upon adsorption of the target analyte, the photodetector response for the green light source gradually starts declining while the response for the red light source starts increasing. Using a ratio of the responses of the first and second light sources is desirable, as it can help reduce the impact of fluctuations in the intensity of light delivered by a light source.

The specific wavelength ranges chosen may depend upon the properties of the particular optical analyte sensor that is used, the particular analyte(s) that is desired to be monitored, etc. In various embodiments, wavelength range A and wavelength range B are chosen such that their centerpoints are at least 20, at least 40, or at least 60 nanometers apart. In further specific embodiments, wavelength range A and wavelength range B are chosen such that their centerpoints are at most 140, at most 120, or at most 100 nm apart. In various embodiments, the center of the first wavelength range may be within about 10 nm, 20 nm, or 40 nm of a peak maximum, and the center of the second wavelength range may be within about 10 nm, 20 nm, or 40 nm of a valley minimum. In some embodiments, optical interrogation may be performed wherein wavelength range A is centered around approximately 520 nm, and wherein wavelength range B is centered around approximately 640 nm. In other embodiments, optical interrogation may be performed wherein wavelength range A is centered around approximately 591 nm, and wherein wavelength range B is centered around approximately 606 nm. As mentioned, interrogation in wavelength ranges A and B may be achieved, e.g., by use of narrowband light sources such as LEDs and the like. In other embodiments, broad-band light sources could be filtered using narrowband or band pass filters to tune the wavelength range to a desired spectral region. In some exemplary embodiments, one or more wavelength ranges can be in the UV or near infra-read regions of the spectrum. PIM optical analyte sensors, for example, exhibit peaks and valleys in those regions and, therefore, one may provide sensor/reader combinations configured to operate in those regions of the spectrum. If desired, additional optical interrogation may be performed at other wavelength ranges. Such additional ranges may be between ranges A and B, overlapping with ranges A and B, or outside ranges A and B. Such additional optical interrogation ranges (which may be provided, e.g., by the use of additional light sources) may provide enhanced resolution, dynamic range, precision, etc.

In such configurations, a signal from a detector indicative of the amount of light detected in wavelength range A can be compared (e.g., ratioed by a microprocessor), to a signal from a detector indicative of the amount of light detected in wavelength range B. Such comparison/ratioing may provide significant advantages. For example, it may allow the confirmation that a new or replacement optical analyte sensor is in operating condition (e.g., has not been prematurely exposed to analyte, damaged, out of alignment, etc.), as further described below. Thus in some embodiments, methods disclosed herein include the step of obtaining an initial compared signal and determining whether the initial compared signal is in an acceptable range. Use of compared (e.g., ratioed) signals may also enhance the dynamic range of the optical reader. In the context of the methods disclosed herein, the comparing of first and second signals (e.g., signals indicative of an amount of light detected in a first wavelength range and a second wavelength range) can include the comparing of averaged signals (e.g., the obtaining of multiple first signals and averaging them and the obtaining of multiple second signals and averaging them, and comparing the averaged first signal with an averaged second signal), as well as the comparing of an individual first signal with an individual second signal.

Figure 6:
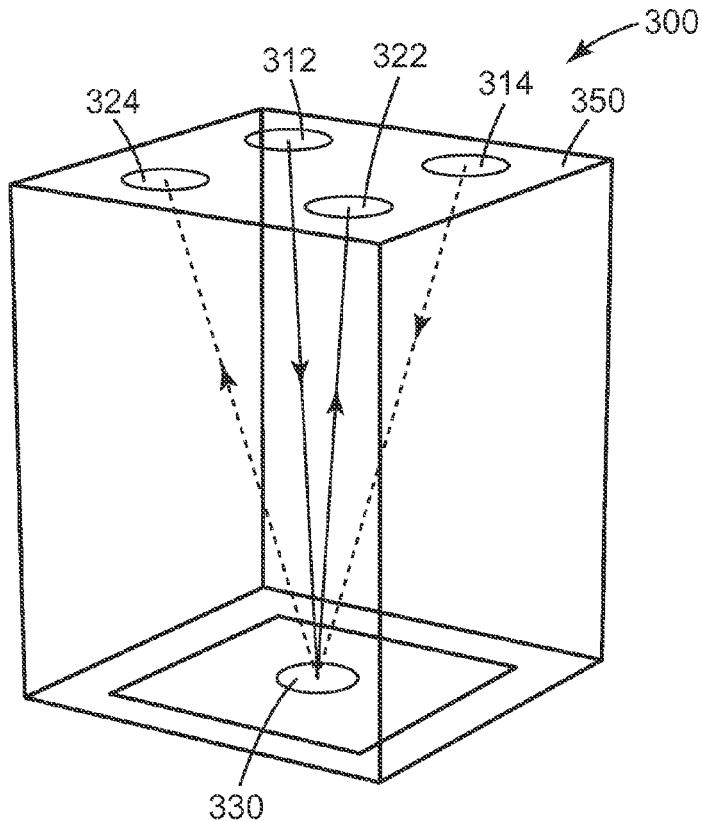
FIG. 6 shows schematically another exemplary embodiment of an optical reader according to the present disclosure.

FIG. 6 shows schematically another exemplary embodiment of an optical reader 300 according to the present disclosure. The optical reader 300 includes two light sources 312 and 314 and two detectors 322 and 324. One or more light sources and one or more detectors can be mounted on the same support 350. Such an optical reader also can be configured to be attached to the housing of a filter system according to the present disclosure, including a optical analyte sensor, such that at least a portion of light emitted by at least one light source 312, 314 is reflected from the optical analyte sensor 330 and captured by the detectors 322 and 324. In this exemplary embodiment, light sources 312 and 314 each may emit light in a different wavelength range with a different peak wavelength than that emitted by the other light source. Each light source 312 and 314 can be used in combination with a photodetector 322 and 324, respectively, designed to detect light in the particular wavelength range emitted by the corresponding light source.

Figure 7A:
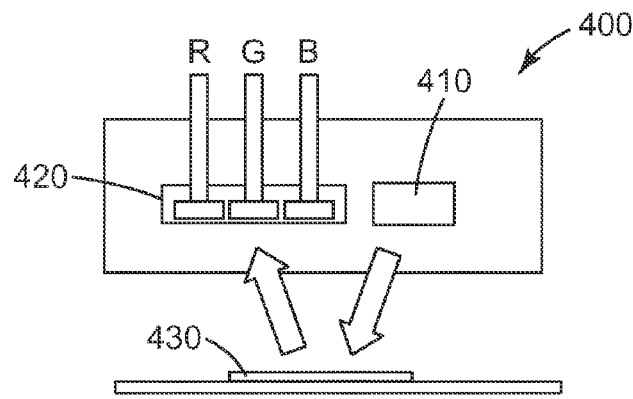
FIG. 7A shows an exemplary embodiment of an optical reader utilizing one or more broadband light sources.

FIG. 7A shows an exemplary embodiment of an optical reader 400 utilizing one or more broadband light sources 410. The broadband light source 410 can be or include one or more broadband light sources, such as white LEDs. When more than one broadband light source is used, at least two of the light sources can be configured to have different spectral ranges and/or profiles, as described above in connection with exemplary embodiments utilizing narrowband light sources. The emission spectra of one or more of the broadband light sources can be tailored simply by purchasing a commercially available light source with a desired spectrum or by placing one or more spectral filters over one or more of the broadband light sources, such as the spectral filters known to those of ordinary skill in the art. A suitable spectral filter may include an optical coating over a transparent substrate. Alternatively, two or more narrow band light sources characterized by different wavelength ranges as well as different peak wavelengths may be used together to simulate a broad band light source. For example, light sources characterized by wavelength ranges and peak wavelengths covering different primary color regions could be used in combination to simulate a while light source. Particularly, one or more of red, green and blue LEDs can be used in combination.

Figure 7B:
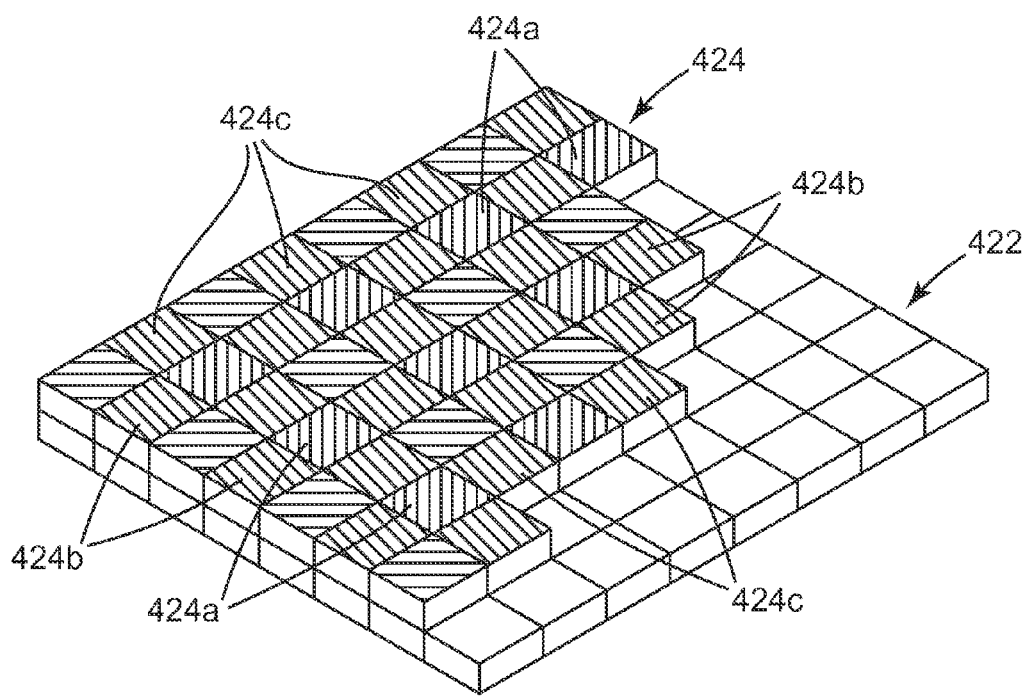
FIG. 7B shows schematically a filter having areas with different spectral transmissions.

Such exemplary embodiments can also include a color-sensing detector 420. Such a detector allows a more direct measurement of the color of the optical analyte sensor, rather than simply a reflectance within a particular spectral range of illumination. A color-sensing detector can be implemented as a multi-pixel photodetector array that includes two or more (preferably, three or more) sets of photodetectors that are sensitive to only two or more (preferably, three or more) different relatively narrow wavelength ranges. In one exemplary embodiment, such a color-sensing photodetector may include banks of red, green, blue and white photodetectors, such as photodiodes. Another exemplary color-sensing detector may include an array of the same or similar photodetectors overlaid with a spectral filter to achieve a similar result. One example of spectral filter suitable for such exemplary embodiments is a filter having areas with different spectral transmissions, such as a tiled spectral filter 424 disposed over a detector array 422, as shown in FIG. 7B. The spectral filter 424 includes areas (tiles) characterized by different spectral transmissions. For example, one or more tiles 424a may be characterized by high transmission of red light, one or more times 424b may be characterized by high transmission of blue light, and one or more tiles 424c may be characterized by high transmission of green light. One example of such a spectral filter is a Bayer filter.

Referring further to FIG. 7A, an optical analyte sensor 430 is illuminated by the light source(s) 410 and the reflected signal is detected by the detector 420. A programmable logic device such as a microprocessor may then decompose the detector optical response into primary colors, such as R, G, B. The decomposed responses can be processed to infer any relevant information (such as whether a change has occurred in at least one of the optical characteristics of the optical analyte sensor 430, whether the reader 400 is in alignment with the sensor 430, etc.) using standard algorithms. In yet other exemplary embodiments, a broadband light source can be used in combination with one or more narrowband detectors. Alternatively, interrogation at a given predetermined wavelength range may achieved by the use of a narrowband light source in combination with a narrowband or broadband detector.

The use of multiple or broadband light sources and/or multiple or broadband photodetectors may allow enhanced operation of the optical reader. For example, such designs may allow the detection of a wider range of detectable analytes, may allow a wider concentration range of analyte to be detected, may allow more precise quantitation of the concentration of analyte, may negate the need to calibrate the optical reader each time that a new or replacement optical analyte sensor is installed, and so on. Thus in some embodiments, performance of the methods described herein does not require that the sensing element is exposed to a calibration gas containing a known non-zero concentration of analyte, prior to the monitoring of an atmosphere potentially containing the analyte. Further, an advantage of using color measurements as described above is that it does not require tailoring the optical analyte sensor for any particular predetermined spectral region.

Figure 8A:
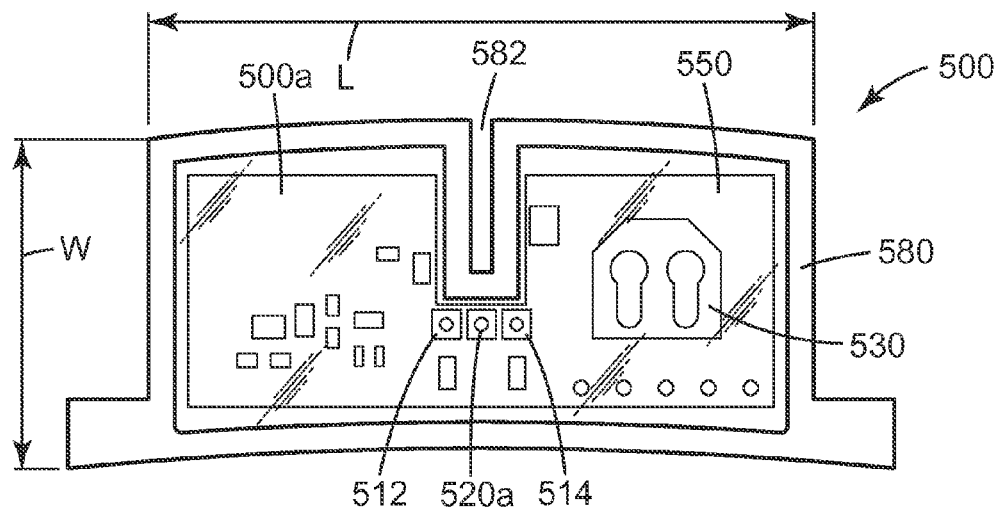
FIGS. 8A and 8B show different sides of an exemplary embodiment of an optical reader according to the present disclosure.
Figure 8B:
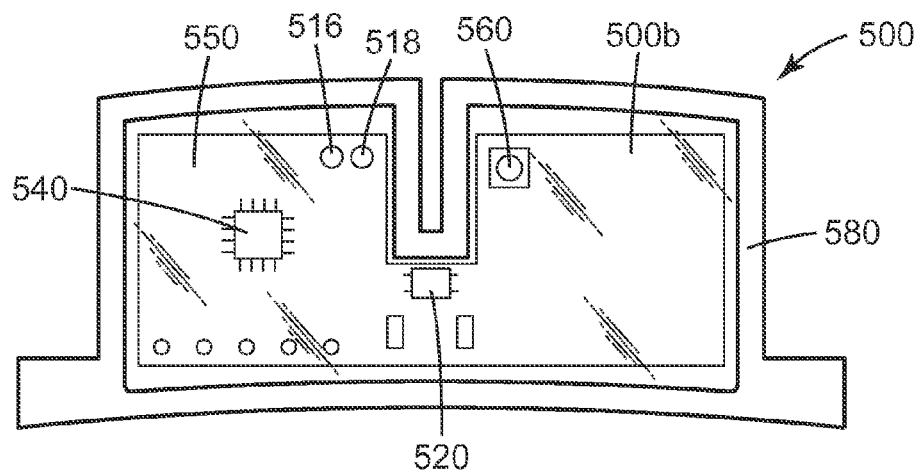

FIGS. 8A and 8B show opposing first and second sides 500a and 500b of another exemplary embodiment of an optical reader 500 according to the present disclosure for interrogating an optical analyte sensor according to the present disclosure. The optical reader 500 includes first and second light sources 512 and 514 and a detector 520. The first light source is characterized by a first spectral profile, and a second light source is characterized by a second spectral profile. For example, the first light source may be characterized by a first peak wavelength and a first wavelength range, and a second light source may be characterized by a second peak wavelength and a second wavelength range. In typical exemplary embodiments, the first spectral profile is different from the second spectral profile. For example, the first and second peak wavelengths and/or the first and second wavelength bands may be different. In this exemplary embodiment, first and second light sources 512 and 514 and a detector 520 can be mounted on the same support 550, such as a printed circuit board. The optical reader may further include a programmable logic device 540, which is preferably also mounted on the support 550.

The optical reader 500 may further include a battery 530, an alerting device, such as one or more light sources 516 and 518, and an actuator 560, all of which are shown in FIG. 8B.

A user may trigger the actuator 560 to initiate the interrogation of an optical analyte sensor by the optical reader 500. The optical reader 500 may be connected to another device, such as a computer by a wireless interface or by a serial interface. Thus, the optical reader may communicate various information to a database or a display, such as data obtained by the optical reader from interrogating an optical analyte sensor according to the present disclosure. Typically, a serial interface is used during testing, qualification, and/or calibration of the optical reader.

Preferably, first and second light sources 512 and 514 are disposed on one side of the support 550, while the detector 520 is disposed on an opposing side of the support 550. In this exemplary embodiment, the support has an opening 520a so that light returning from the optical analyte sensor could reach the detector 520. Light sources can be mounted on (e.g., attached to) a printed circuit board at an angle relative to printed circuit board, so as to establish the desired angle between light source(s), detector and optical analyte sensor. If one or more light sources are light-emitting diodes, they may be electrically connected to printed circuit board via any known mounting method. Through-hole methods may be better able to establish the desired angle, although surface mount methods may be used if desired. If desired, one or more positioning devices (e.g., holders, collars, etc.) may be used to position one or more light sources on the printed circuit board at the desired angle.

One or more of the above-referenced components of the optical reader may be disposed in an interior of a housing 580. Preferably, at least first and second light sources 512 and 514, the detector 520, and the support 550 are disposed in the interior of the housing. However, any number of components of the optical sensor 500 may be enclosed in the housing 580, and, in some cases, all of its components. Optical reader housings according to the present disclosure may be constructed with materials transparent for light of the visible spectrum, such as glass or transparent plastics, e.g., polycarbonate, nylon, polystyrene. Alternatively, an optical reader housing can be made from an opaque material with a transparent portion disposed over the detector and one or more light sources, such that the optical reader would be capable of irradiating and receiving light from an optical analyte sensor it is configured to read. The shape of the housing may be any shape suitable for a filter system it is intended to be used with. In yet other exemplary embodiments, the housing may be or include a portion opaque to light of visible spectrum but transparent to light of other spectral regions, such as one or more where infrared or near infrared light sources and detectors are used.

In typical embodiments of the present disclosure the housing includes a registration feature 582 (here, a slot) configured to align the optical reader 500 with an optical analyte sensor, as is explained in detail below. The size and shape of the registration feature may vary depending on the application. In some exemplary embodiments, more than one of the same or different registration features may be included in an optical reader. The optical reader can be configured to be attached to the housing of a filter system according to the present disclosure including an optical analyte sensor, such that at least a portion of light emitted by at least one light source 512, 514 is reflected from an optical analyte sensor it is designed to interrogate and captured by the detector 520. The construction of the exemplary embodiment illustrated in FIGS. 8A and 8B enables one to make use of surface mount optics to arrive at a thin and small form factor reader capable of being held on or at the surface of a filter system such as a filter cartridge as shown and described below. In typical embodiments, the optical reader is very compact and low profile. For example, an optical reader such as the reader shown in FIGS. 8A and 8B may have a typical length L of 20 mm, 60 mm, 100 mm, 150 mm, or any number between any of these values. A typical width W of such an optical reader may be 10 mm, 30 mm, 40 mm, 70 mm, or any number between any of these values. A typical weight of optical readers according to the present disclosure may be 5 g, 8 g, 50 g, 100 g, or any number between any of these values.

Figure 9A:
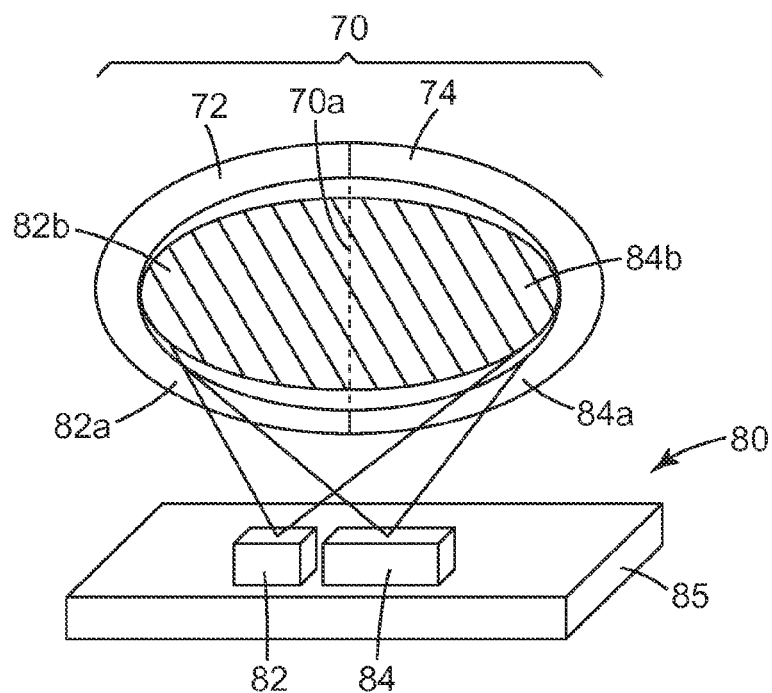
FIG. 9A shows an exemplary optical reader according to the present disclosure, which is configured to interrogate a patterned optical analyte sensor.

FIG. 9A shows an exemplary optical reader 80 according to the present disclosure, which is configured to interrogate a patterned optical analyte sensor 70 having a first region 72 that exhibit a first response to an analyte of interest and a second region 74 that exhibit a second, different, response to an analyte of interest. In some exemplary embodiments, the first response is greater than the second response. Such exemplary patterned sensors are described, for example, in reference to FIG. 3B of the present disclosure. In this particular exemplary embodiment, the first region 72 is configured to serve as a reference, i.e., it does not exhibit a significant (preferably, detectable) response to an analyte of interest. In the second region 74, however, exhibits a change in at least one of the optical characteristics of the optical analyte sensor 70 in response to an analyte of interest.

The optical reader 80 includes at least one light source 82 and at least one detector 84. The optical reader 80 is configured such that, when it disposed in proper alignment to interrogate the optical analyte sensor 70, it can be considered to interrogate the optical analyte sensor 70 in both the first region 72 and the second region 74. In one embodiment, the light source 82 and the detector 84 each have a projection of light area 82b and detection area 84b, respectively, as illustrated in FIG. 9A. The areas 82b and 84b are determined by the solid angle of light 82a emitted by the light source 82 and the solid angle of detection 84a, usually set or designed by the manufacturer. By choosing the opto-electronics with suitable solid angles and by carefully placing them on a support 85, such as a PCB, one can design an optical reader with interrogation capabilities illustrated in FIG. 9A. If the light source 82 and the detector 84 are at the border 70a between the first and second regions 72 and 74, by varying the separation distance between the reader and the sensor, and the distance between the light source and the detector, one can increase or decrease the surface area on the patterned film that the light source illuminates and that the detector captures light from.

Preferably, a half of the area 82b, 84b (which areas may or may not coincide) would be in the first region 72 of the optical analyte sensor 70 and the other half of the area 82b, 84b would be in the second region 72 of the optical analyte sensor 70. Generally, at least a portion of light emitted by the light source 82 is reflected from the first region 72 and captured by the detector 84. Similarly, at least a portion of light emitted by the light source 82 is reflected from the second region 72 and captured by the detector 84. Thus, the light 84a received by the detector 84 would be the sum of light received from the first and second regions 72 and 74. For an optical analyte sensor that has not been exposed to an analyte of interest, the detector response to both the first and second regions 72 and 74 would be similar. However, upon exposure, as at least one of the regions 72 and 74 begins to experience a change in at least one of its optical characteristics, detector reading will change accordingly.

Figure 9B:
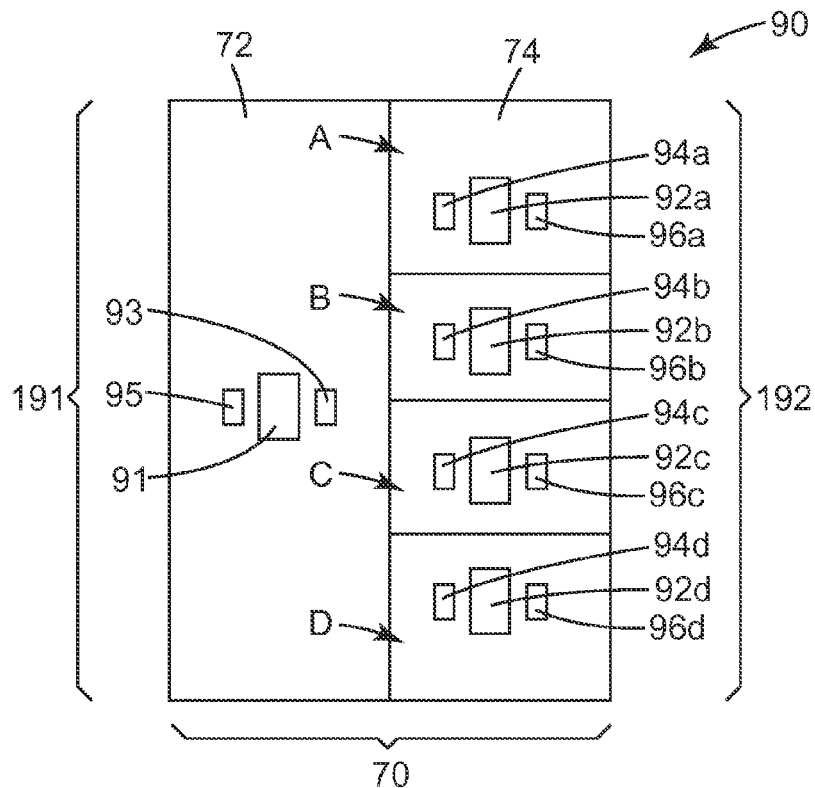
FIG. 9B shows another exemplary optical reader according to the present disclosure, which is configured to interrogate a patterned optical analyte sensor.

Another exemplary optical reader according to the present disclosure is shown in FIG. 9B, which shows an optical reader 90, configured to interrogate a patterned optical analyte sensor 70 having a first region 72 that exhibit a first response to an analyte of interest and a second region 74 that exhibit a second, different, response to an analyte of interest. The change in at least one of the optical characteristics of the optical analyte sensor 70 in response to an analyte of interest may be detected by one or more detectors 92a-92d.

The optical reader 90 includes a first assembly 192 and a second assembly 191. With respect to the illustrated embodiment, the first assembly may be referred to as the sensing assembly and the second assembly may be referred to as the reference assembly. The reference assembly includes one or more (here, two) light sources 93, 95 and one or more (here, one) detectors 91. The optical reader 90 is configured such that, when it disposed in proper alignment to interrogate the optical analyte sensor 70, at least a portion of light emitted by at least one light source 93, 95 is reflected from the first region 72 of the optical analyte sensor 70 and captured by the at least one detector 91. The sensing assembly 192 includes one or more blocks of one or more light sources and one or more detectors. In this exemplary embodiment, the sensing assembly 192 includes four blocks, each block including two light sources 94a-d and 96 a-d and a detector 92a-d. The optical reader 90 is configured such that, when it disposed in proper alignment to interrogate the optical analyte sensor 70, for each block of the sensing assembly 192, at least a portion of light emitted by at least one light source 94a-d, 96a-d is reflected from a particular area (A-D) of the second region 74 of the optical analyte sensor 70 and captured by the at least one detector 92a-d. In particular, at least a portion of light emitted by the first block first and second light sources 94a and 96a reflected from a first area A of the second region 74 of the optical analyte sensor 70 is captured by the first block detector 92a; at least a portion of light emitted by the second block first and second light sources 94b and 96b reflected from a second area B is captured by the second block detector 92b; at least a portion of light emitted by the third block first and second light sources 94c and 96c reflected from a third area C is captured by the third block detector 92c; and at least a portion of light emitted by the fourth block first and second light sources 94d and 96d reflected from a fourth area D is captured by the fourth block detector 92d.

Preferably, the first, second and fourth blocks are positioned over the Areas A, B, C and D of the optical analyte sensor 70, such that there is no overlap between the areas interrogated by the different blocks. In such exemplary embodiments, as an analyte of interest propagates through a filter medium that is in fluid communication with an optical analyte sensor according to this exemplary embodiment, the regions A, B, C and D of the second, responsive, region 74 of the optical analyte sensor 70 will be sequentially exposed to the analyte and, therefore, sequentially undergo a change in at least one optical property. In particular if the optical change is experienced first by the area A, then B, then C, and, finally, D, then the first, second, third and fourth blocks of the sensing assembly 192 will detect the sequential change in the same order. Thus, the present exemplary embodiment allows for a multi-step indicator. For example, one such positioning would provide indication of 100%, 75%, 50%, 25%, and 0% remaining service life respectively.

Although four blocks are shown in the sensing assembly and one block is shown in the reference assembly, any other suitable number of blocks may be used consistently with the present disclosure. Light sources, detectors, optical analyte sensors, and other components and devices suitable for use in this exemplary embodiment may be any suitable system, element or assembly described above or any other suitable system, element or assembly.

Upon interrogation of an optical analyte sensor using methods and devices disclosed herein, a signal may be obtained that is related to the presence and/or concentration of an analyte of interest. In some embodiments, the signal generated by the at least one photodetector of the optical reader is an electrical signal, e.g., in the form of a voltage or current. Such a signal can then be manipulated, processed, etc. Optical readers according to the present disclosure may include one or more analog to digital converters that can provide the signal in a digital form for ease of processing by a programmable logic device, such as a microcontroller, microprocessor or a field programmable gate array, in the event that the signal is initially in an analog form. In case of multiple detectors, a separate signal may be provided by each detector.

Figure 10:
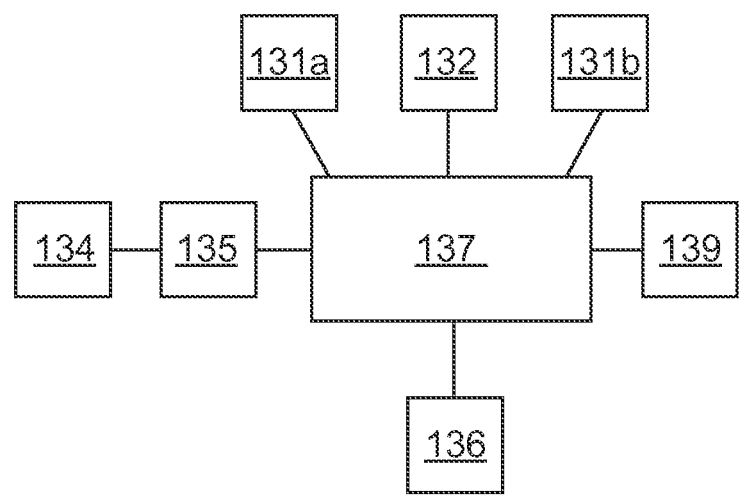
FIG. 10 is a diagram illustrating the operation of optical readers according to the present disclosure.

The signals received from the one or more photodetectors can be mathematically manipulated (individually or in combination) according to algorithms resident in the circuitry of the optical reader (e.g., loaded into software or firmware) as desired. Thus, the optical reader may comprise such components, circuitry, etc., as needed to perform such desired signal processing, and also as needed to control the light source(s) and/or photodetector(s). With reference to the block diagram of FIG. 10, optical readers of the present disclosure may include a programmable logic device, such as a microcontroller, microprocessor or a field programmable gate array, 137 that may operate light source(s) 131 and operate (and receive signals from) photodetector(s) 132, may process, manipulate, etc., signals received from photodetector(s) 132, may hold various data and parameters in memory, may operate an alerting device 136, such as an indicator or a display, and communicate with a user via an interface 139, such as a wireless or serial interface, may receive power from (internal or external) power source 134 via power supply 135, and may carry out other functions as needed.

For example, signals collected from photodetector 132 may be held resident in memory (e.g., of microprocessor 137) so that the time-dependent history of the signals may be accessed and consulted. This may be useful, for example, in a case in which (e.g. in the presence of a certain amount of analyte) a second peak in the optical analyte sensor reflectance spectrum shifts sufficiently close to the A wavelength range that a signal is received in the A wavelength range resulting from a peak that is similar to that initially received from a first peak in the absence of analyte. By following the time-dependent history of the signals received from photodetector 132 (e.g., the signal in wavelength range A falling, then rising again towards its initial value) embodiments of the present disclosure might be able to distinguish such a condition (e.g., perhaps caused by a very large amount of analyte) from a condition in which a relatively constant reflected light signal is received over the time period of the potential analyte exposure. Similar signal processing may be performed when using compared (e.g., ratioed) signals.

Other information may be held resident in memory of microprocessor 137 to provide enhanced functioning of exemplary embodiments of the present disclosure. For example, information regarding one or more predetermined conditions to which a signal from one or more detectors may be compared (e.g., a predetermined response curve, empirically derived or obtained via exposure of a sensing element to known analyte concentrations) may be provided that relates a signal (e.g., the intensity of light at wavelength range A); or, a compared signal (e.g. the ratio of the intensity of light at wavelength range A to that at wavelength range B), etc., to a concentration of analyte in a monitored environment. Exemplary embodiments can thus function by correlating a compared signal to a predetermined response curve so as to obtain a concentration value that is associated with, or representative of, the concentration of an analyte. A single response curve may be preloaded (e.g., permanently) into the memory of an exemplary embodiment; or, response curves may be uploaded periodically into the memory for use with particular designs of optical analyte sensors, particular analytes, and so on. Multiple response curves may be used. In the context of the methods disclosed herein, such correlating of a compared signal with a response curve encompasses the correlating of an averaged compared signal (e.g., resulting from the obtaining of multiple compared signals and averaging them), as well as the correlating of an individual compared signal. Correlation of signal obtained by the detector with a threshold maintained in memory can also allow users to set their own criteria for triggering a particular response, such as a visual or audible indication, data logging, etc. In environments with highly toxic contaminants, for example, a user may want the sensor to respond to very low concentrations and can set this threshold accordingly. In contrast, a low toxicity contaminant may not require a threshold to be set as low.

In summary, embodiments of the present disclosure, based on the signals received and/or processed as described herein, may produce, via an alerting feature, a notification signal that is associated with, e.g. representative of, the presence of an analyte of interest at a specific location in the sorbent bed. The notification signal can be communicated to a user of exemplary embodiments of the present disclosure by an alerting feature (for example, by a visual, audio, or tactile signal). In one embodiment, the notification signal can be an actual numerical value of the concentration of the analyte. In addition to this, and/or instead of this, and notification signal can be provided that, while not a numerical value, is associated with such a numerical value. For example, embodiments of the present disclosure may provide an auditory signal (e.g., a beep, chirp, alarm signal), a visual signal, such as one or more light indicators, and/or a vibrational signal, upon the detection of the analyte, and/or of the detection of a certain amount of the analyte. In some exemplary embodiments, the alerting device may be capable of providing at least one of a visual and audible indication. In one embodiment, the alerting device includes one or more flashing lights and/or light indicators of different colors (e.g., green light to show the optical reader is working and red to indicate a particular condition).

Some embodiments of the present disclosure may provide nonquantitative indications, (for example, indicating whether an analyte of interest is present, e.g., above a certain concentration). Some embodiments may provide semiquantitative and/or quantitative information (e.g., an estimate or indication of the concentration of the analyte). Some embodiments may provide a cumulative indication (that is, an integrated indication that arises from the concentration of analyte in the monitored air over a period of time that may range up to a few hours). This type of indication is useful to relate the progression of a contaminant through the filter system to the user. In some other embodiments, embodiments of the present disclosure may provide periodic or even "real time" readings. In some embodiments, exemplary embodiments of the present disclosure may communicate, either in real time or periodically (e.g. by transmission of datalogged information), such information to a receiving station or a remote device, such as a database. For example, exemplary embodiments of the present disclosure may transmit such information (e.g., by wireless or infrared transmission) to a computer, workstation, central processing facility, or the like. Wireless interface included on an embodiment of the invention can provide a seamless and transparent way of communicating the real time or periodic status updates of the filter system to a user via a wireless display or to a supervisor or industrial hygienist.

FIGS. 11A, 11B, 11C and 11D show another exemplary filter system 600 according to the present disclosure. This exemplary filter system is a filter cartridge 600, which may be used in turbo units of PAPRs, such as the turbo unit 14 described in connection with FIG. 1. The filter cartridge 600 includes a housing 620 and a filter medium 622, such as a sorbent material, e.g., activated carbon, disposed within the housing 620. An optical analyte sensor 628 is also disposed within the housing 620 in fluid communication with the filter medium 622. As explained above, the optical analyte sensor 628 may include a detection medium that changes at least one of its optical characteristics in response to an analyte, and it is disposed within the housing 620 such that the detection medium is in fluid communication with the filter medium 622. A wall 626 of a housing 620 includes a viewing port, such as a transparent portion 627 through which the optical analyte sensor 628 may be interrogated.

Figure 11A:
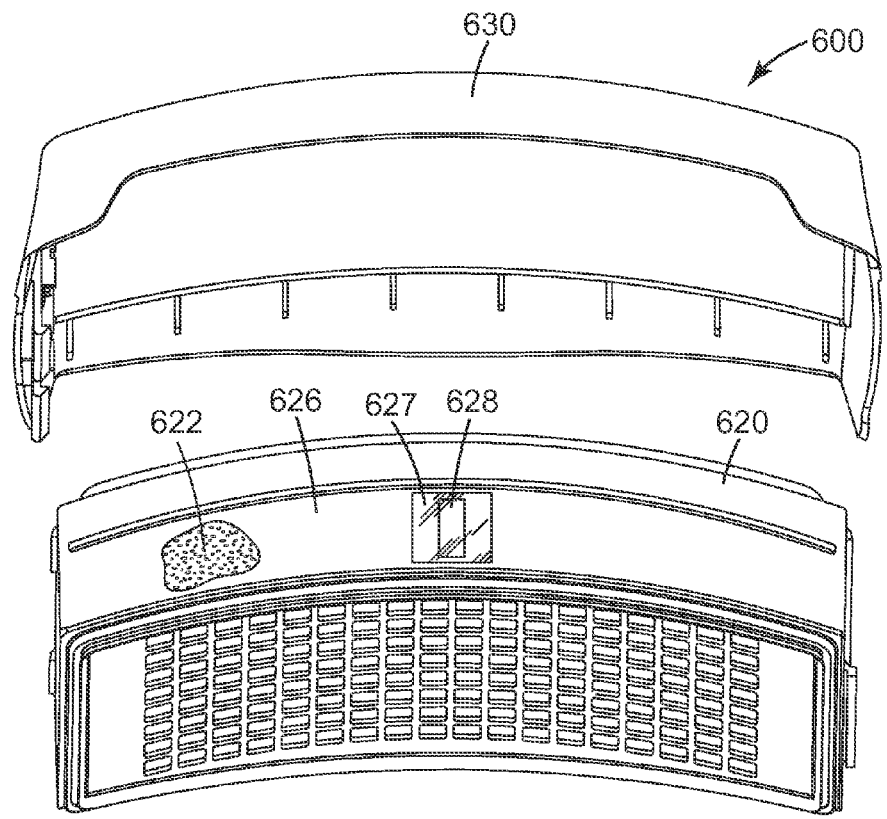
FIGS. 11A-11D show schematically another exemplary filter system according to the present disclosure and some exemplary components of such a filter system.
Figure 11B:
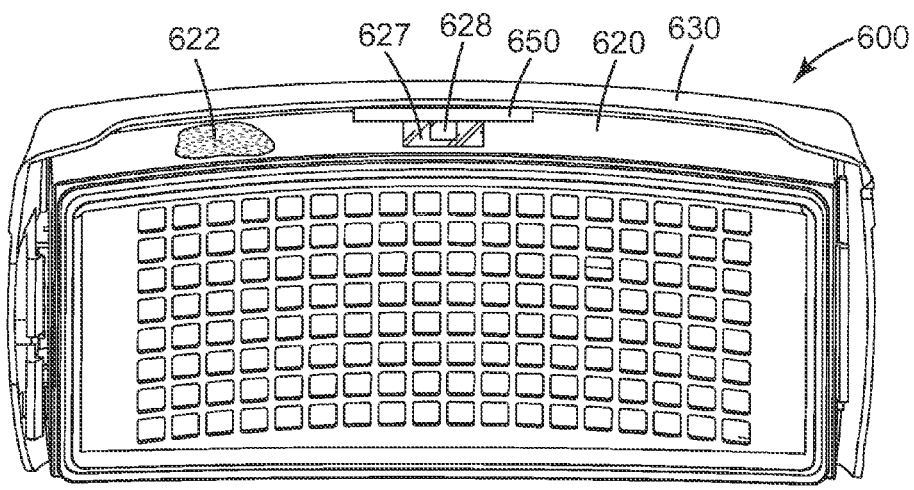

The filter system 600 further includes a removable housing portion 630 that is capable of being removably attached to the housing 620. Although in FIGS. 11A-11D the removable housing portion 630 is shown as a structure encircling the outer wall 626 of the housing 620, the removable portion can take on a variety of other suitable shapes. In some embodiments, the removable housing portion may be in the form of a collar or skirt, or a cover or cap. FIG. 12 shows an alternative embodiment of a removable housing portion 635 according to the present disclosure, which is shaped as a cover or cap. An optical reader 655 may be permanently or removably attached to the removable housing portion 635 or to the filter housing in the same manner as described in connection with the removable housing portions according to the present disclosure. In other exemplary embodiments, the removable housing portion may only partially encircle or cover the housing, e.g., the removable housing portion may encircle only a portion of the outer wall 626 of the housing 620. Other configurations are also within the scope of the present disclosure.

Figure 12:
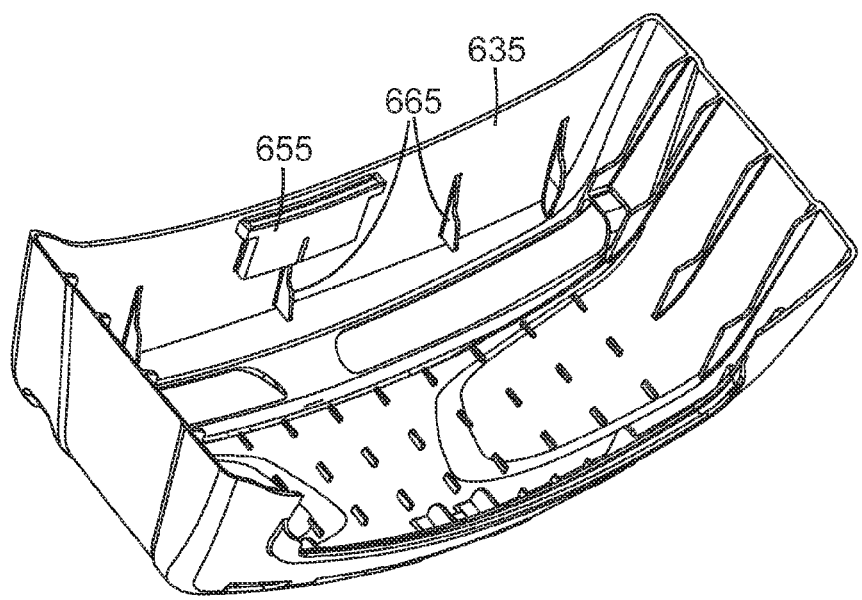
FIG. 12 shows an embodiment of a removable housing portion according to the present disclosure.
Figure 13A:
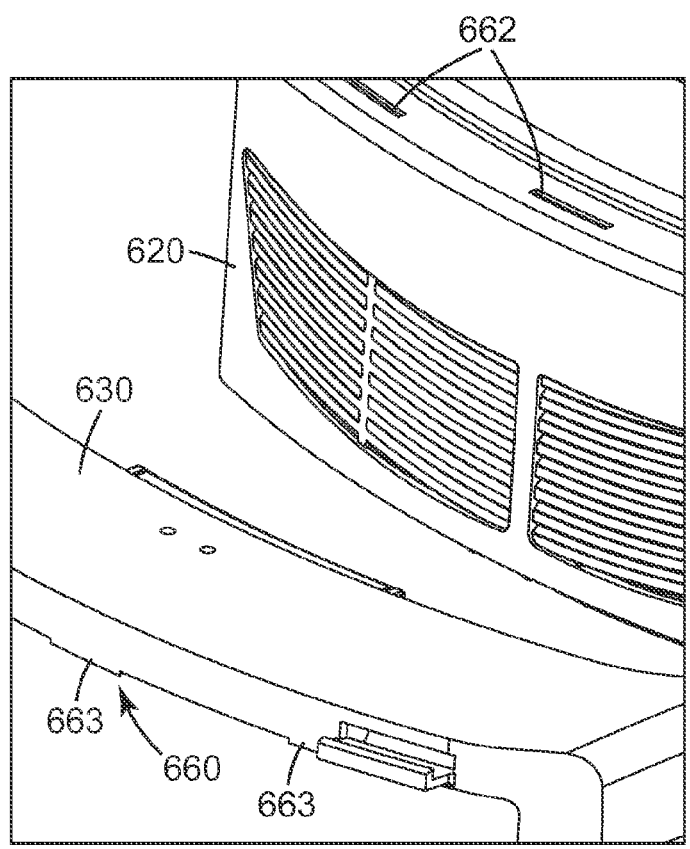
FIGS. 13A and 13B show exemplary embodiments of attachment mechanisms.
Figure 13B:
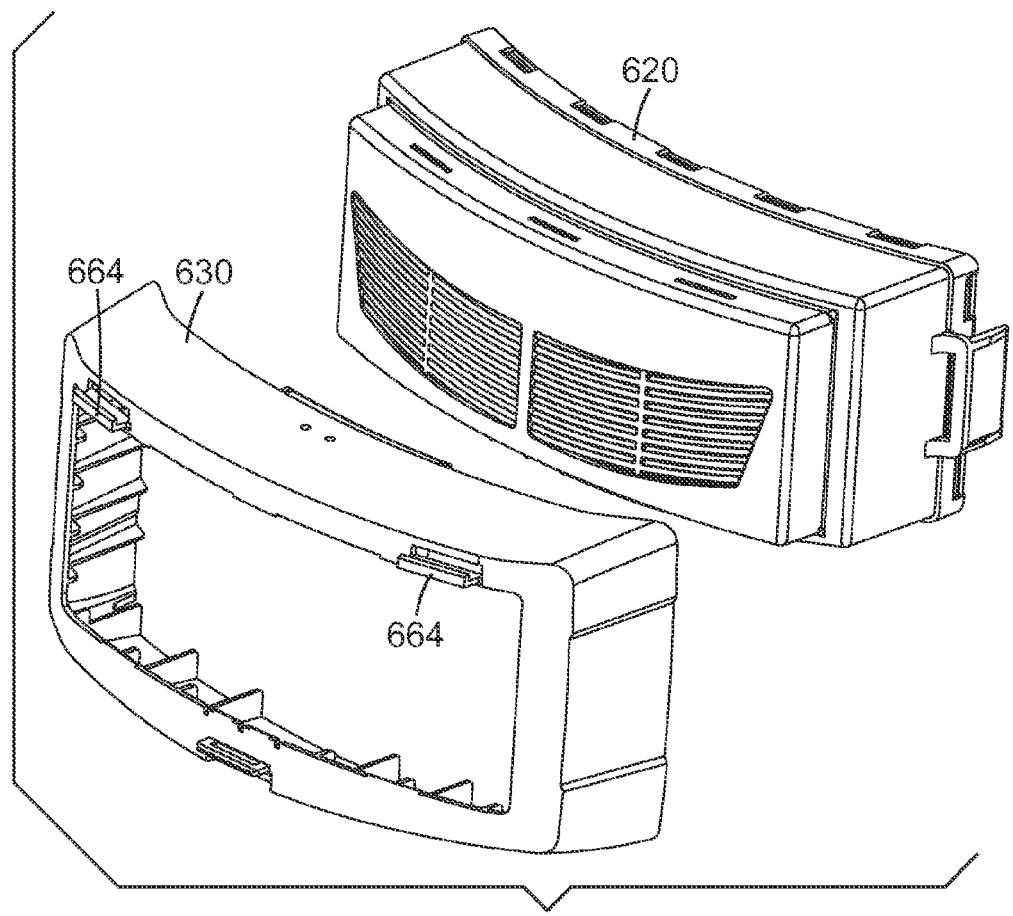

The removable attachment of the housing portion 630 to the housing 620 may be effectuated by any suitable attachment mechanism, such as one or more resilient snap-fit features. FIG. 13A shows one exemplary embodiment of an attachment mechanism 660, which includes one or more tabs 663 and one or more mating slots 662. Although the figure shows the tab being a part of the removable housing portion 630 and the slot being a part of the housing 620, the location of the features could be reversed and changed in any suitable way. Another exemplary embodiment of an attachment mechanism is illustrated in FIGS. 12 and 13B. FIG. 12 shows one or more (preferably, plurality) of beveled ribs 665, which are configured to be engaged by one or more (preferably, plurality) of hooks 664. Other suitable attachment mechanisms may include one or more latches (such as a latch described in connection with FIGS. 18A and 18B), threaded features, or separate engagement parts such as screws, nuts or clips engaging the housing 620 and the housing portion 630. Thus, in some exemplary embodiments, when the filter cartridge is expired, attachment features according to the present disclosure allow one to readily detach the removable housing portion and retain it for use on succeeding filter cartridges. In other exemplary embodiments, the housing portion 630 may be permanently attached, for example, by adhesive.

With further reference to FIGS. 11A to 11D, the filter system 600 includes an optical reader 650. The optical reader, including its circuitry and power source, can be permanently or removably attached to the housing portion 630 or to the filter housing in the same manner as described in connection with the removable housing portions according to the present disclosure. The housing portion 630, in turn, may be permanently or removably attached to the housing 620. As described above, the optical reader 650 may include at least one light source and at least one detector. The optical reader then should be attached to the removable housing portion 630 such that, when the removable housing portion 630 is attached to the housing 620, at least a portion of light emitted by at least one light source is reflected from the optical analyte sensor 628 and captured by at least one detector.

In the illustrated embodiment, the optical reader 650 is disposed between the removable housing portion 630 and the optical analyte sensor 628. However, in other exemplary embodiments, some portions or components of the optical reader 650 may be disposed outside of the removable housing portion 630. For example, the removable housing portion 630 may include one or more openings 632 and 634. At least one such opening may be disposed over the optical reader 650. This may be useful if the optical reader 650 includes an alerting device with a visual indicator visible through at least one of the openings.

In some exemplary embodiments, the optical reader 650 can be caused to interrogate the optical analyte sensor 628, and, optionally, provide the above-referenced indication, upon actuation by a user, such as via a push button. A user actuator (such as an actuator described in connection with FIGS. 8A and 8B) operatively connected with the optical reader may be accessible to a user through one of the openings 632 and 634. Thus, in such exemplary embodiments, upon user actuation of the optical reader 650, a spectrum of light captured by at least one detector of the optical reader 650 can be analyzed for a change in at least one of the optical characteristics of the detection medium of the optical analyte sensor 628. The optical reader 650 can then provide an indication to a user if the change in at least one optical characteristic meets a predetermined condition.

In typical embodiments of the present disclosure, with an optical reader having at least one light source and at least one detector, the optical reader is attached (permanently or removably, via a housing portion or directly) to the housing of a filter system, such as a filter cartridge, such that at least a portion of light emitted by at least one light source is reflected from the optical analyte sensor and captured by at least one detector. To aid in aligning the optical reader in such a manner, at least one of the optical reader and the housing or the removable housing portion (whichever the optical sensor is disposed on) includes at least one registration feature. In typical embodiments of the present disclosure, each of the optical reader and the housing or removable housing portion have a registration feature that mates with a corresponding feature on a connecting part.

Figure 11C:
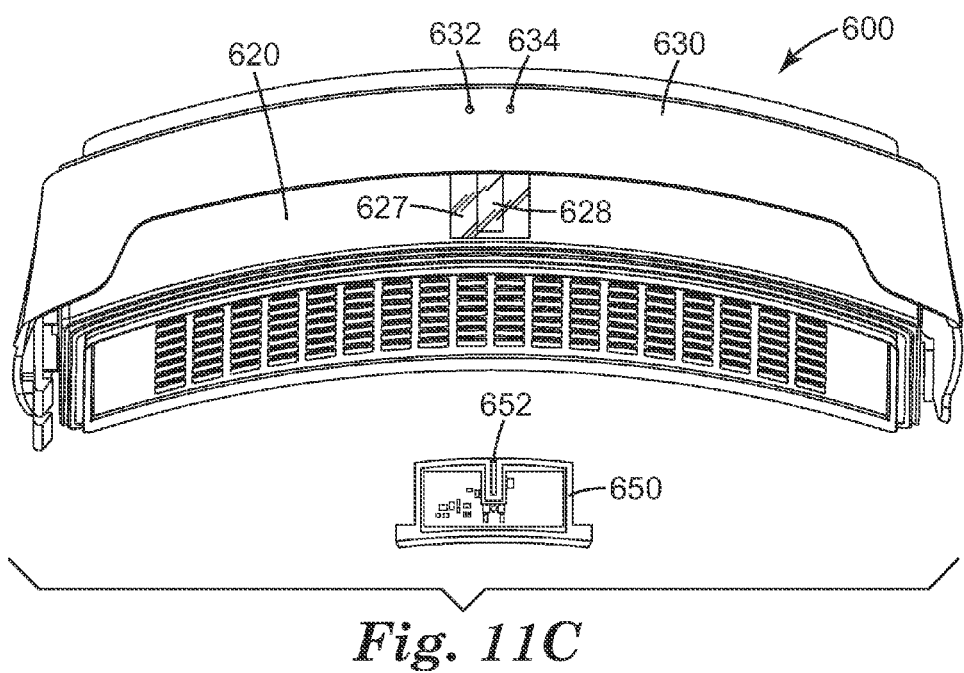
Figure 11D:
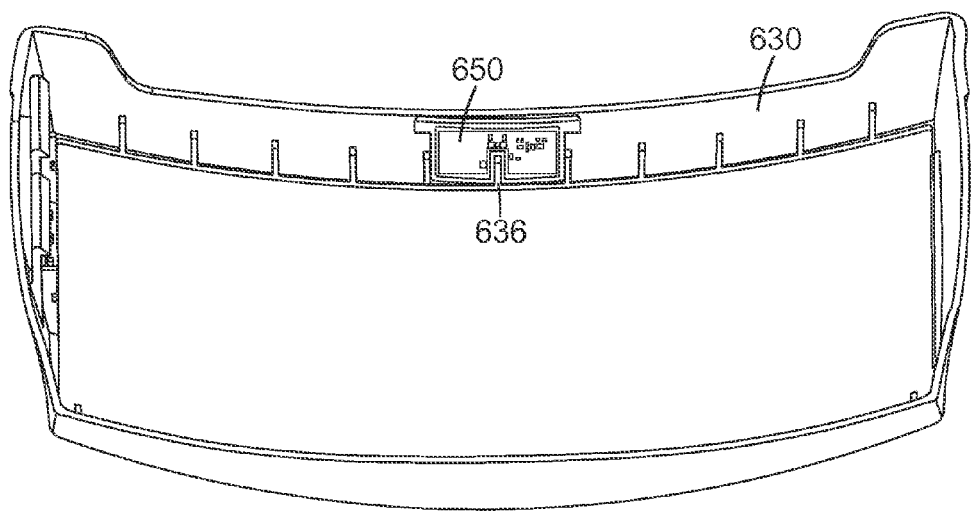

In particular, FIGS. 11C and 11D show that a registration feature 652 of the optical reader 650 may be a slot, while a registration feature of the removable housing portion 630 may be a rib 636. As illustrated in FIG. 11D, the registration features 652 and 636 can be mated to achieve a proper alignment of the optical reader 650 and the optical analyte sensor 628, when the filter system 600 is assembled as shown in FIG. 11B.

Figure 14A:
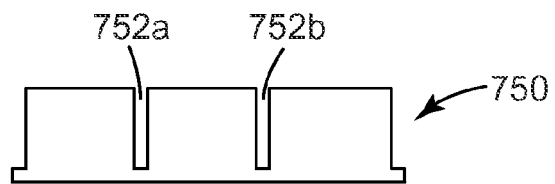
FIG. 14A-14C show schematically different types of registration features.
Figure 14B:
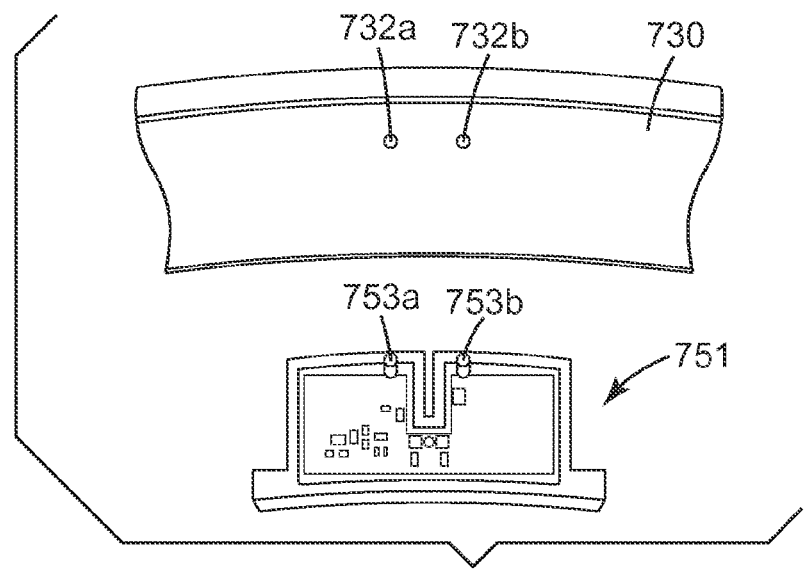
Figure 14C:
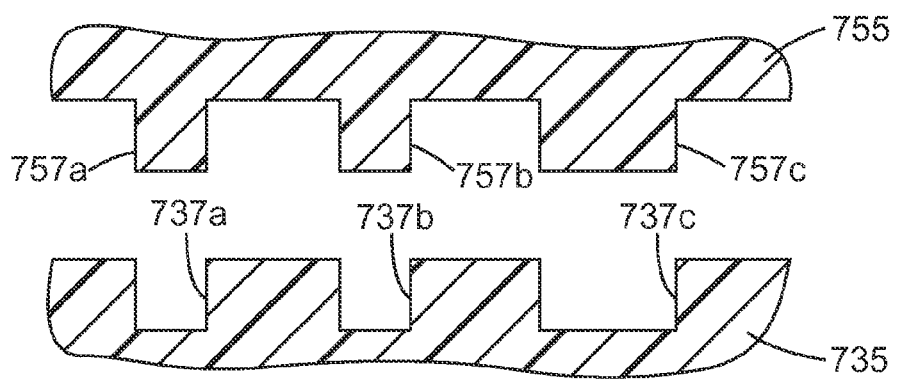

A variety of other types of registration features may be used consistently with the present disclosure, such as mating protrusion(s) and depression(s), tab(s) and slot(s), etc. For example, FIG. 14A shows an optical reader 750 having registration features 752a and 752b. Mating registration features, such as ribs (not shown) would be provided on a removable housing portion or the housing. Other configurations are also within the scope of the present disclosure, including slots of different shapes and sizes, other types of depressions or protrusions, snaps, etc. FIG. 14B shows another exemplary embodiment of one or more registration features. In particular, optical reader 751 includes one, two or more posts 753a, 753b configured to mate with one, two or more openings 732a, 732b of a removable housing portion 730, a housing itself, of another suitable component. FIG. 14C shows another exemplary embodiment of one or more registration features. In particular, FIG. 14C illustrates a portion of an optical reader 755 including one or more rails 757a, 757b, and 757c, which are configured to mate with corresponding grooves 737a, 737b and 737c of a removable housing portion 735, a housing itself, of another suitable component. Two, three or more rails and the corresponding grooves may be different in size to ensure that the orientation of the optical reader not be reversed. For example, as shown in FIG. 14C, rail 757b is wider than rail 757a, and rail 757c is wider than rail 757b.

Exemplary systems according to the present disclosure may further include a method or mechanism for confirming the alignment of the optical reader with the optical analyte sensor before the filter system is used. For example, once the optical reader is mounted onto a filter system such that the optical reader is over an optical analyte sensor, alignment can be diagnosed by determining how much light is received by the detector, comparing it to a threshold value, and if the amount of light received by the detector is below a certain threshold, the optical reader may be deemed to be out of alignment. This feature can be accomplished, for example, using an optical reader as illustrated in FIGS. 8A and 8B. In addition to the features described above, the optical reader 500 would further include an alignment indicator (such as the one or more indicators 516 and 518). Alternatively, separate alignment indicator(s) may be provided.

Generally, during a diagnostic sequence, light from one or more light sources 512 and 514 would reflect off an alignment feedback feature (for example, an optical analyte sensor under test according to any exemplary embodiment) and be detected by the detector 520. Although the alignment feedback feature is exemplified as an optical analyte sensor, it can also be a feature separate from (and additional to) an optical analyte sensor, such as any specularly or diffusely reflective feature, for example, a reflective or white film, tape, sticker or dot. The detected signals may be analyzed and compared to one or more predetermined parameters or criteria indicative of proper alignment, such as the amount of light received by the detector and/or its spectral characteristics. The optical reader is then deemed to be out of alignment, if the detected signals do not meet at least one criterion indicative of proper alignment.

In one embodiment, alignment indicator may provide an indication that the optical reader is disposed over an optical analyte sensor, such as a blinking light. The detector 520 would measure an amount of light from both light sources 512 and 514 reaching and reflected from the optical analyte sensor. If the optical reader is aligned properly, the detector 520 would see responses for both light sources to be similar or of a predetermined ratio with a nominal error %. Alignment indicator may then provide an indication of proper alignment, for example, by stopping blinking and turning on steady for few seconds. If the detector detects that a signal from one or both of light sources does not correspond to a predetermined value, an indication of misalignment will be provided. For example, alignment indicator may continue blinking rapidly. In other exemplary embodiments, alignment testing may be performed with a separate (additional) light source(s) and/or detector(s) than the light sources 512, 514 and a detector 520.

Figure 15:
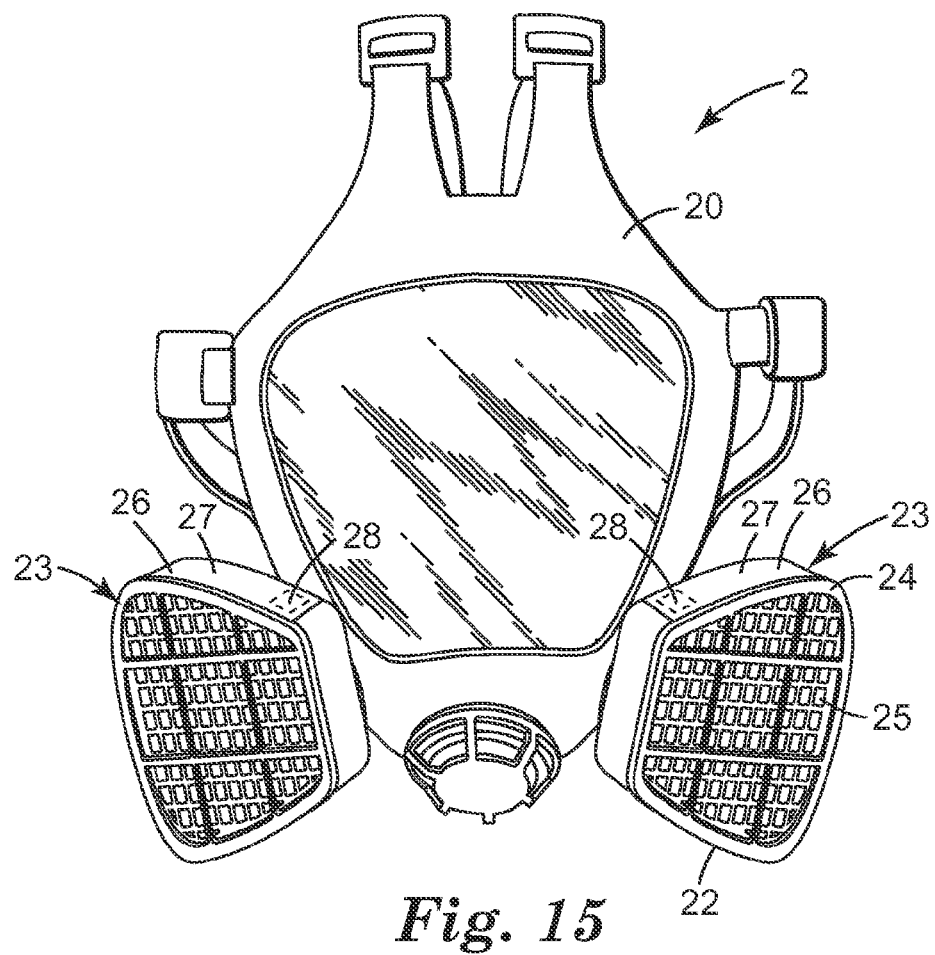
FIG. 15 shows yet another embodiment of a filter system according to the present disclosure.

FIG. 15 shows another embodiment of a filter system according to the present disclosure—a personal respirator 2 including a respirator cartridge 23. The exemplary personal respirator 2 includes a face mask 20 on which a pair of air purifying respirator cartridges 23 may be mounted, although the number of cartridges may vary. For example, some embodiments may include only one cartridge. One or more cartridges 23 may be removable with respect to the face mask 20 and replaceable. One or more cartridges 23 includes a housing 22 and a filter medium 21 (shown in FIG. 16), such as a sorbent material, e.g., activated carbon, disposed within the housing 22. An optical analyte sensor 28 including detection medium (not shown) is also disposed within the housing 22 such that the detection medium is in fluid communication with the filter medium. The exemplary housing 22 includes a front cover 24 that has a plurality of openings 25 that may serve as gas inlets, permitting ambient air from the external environment to flow into cartridge 23, through the filter medium and thence through a passage (not shown) that serves as a gas outlet from cartridge 23 and an inlet to face mask 20. Exhaled air exits respirator 2 through an exhalation valve.

A wall 26 of a housing 22 may include a transparent portion 27 (which is transparent for the particular spectral range to which the light source(s) and the detector(s) are tuned) through which the optical analyte sensor 28 may be read by an optical reader 29. Alternatively, the entire wall 26 may be transparent. The optical analyte sensor 28 may be included in one or more of the cartridges 23. As in the previously described embodiments, optical analyte sensor 28 is optically responsive, for example, by undergoing a change when the filter medium becomes equilibrated with an analyte at the conditions of exposure. In particular, the detection medium of the optical analyte sensor may change at least one of its optical characteristics in response to the analyte, which change is detected by the optical reader. This information may be used in a variety of ways, including processing, storing, and communicating it to the wearer or another individual, possibly aiding such individual(s) in recognizing that it is time to replace the cartridge or cartridges 23.

Figure 16:
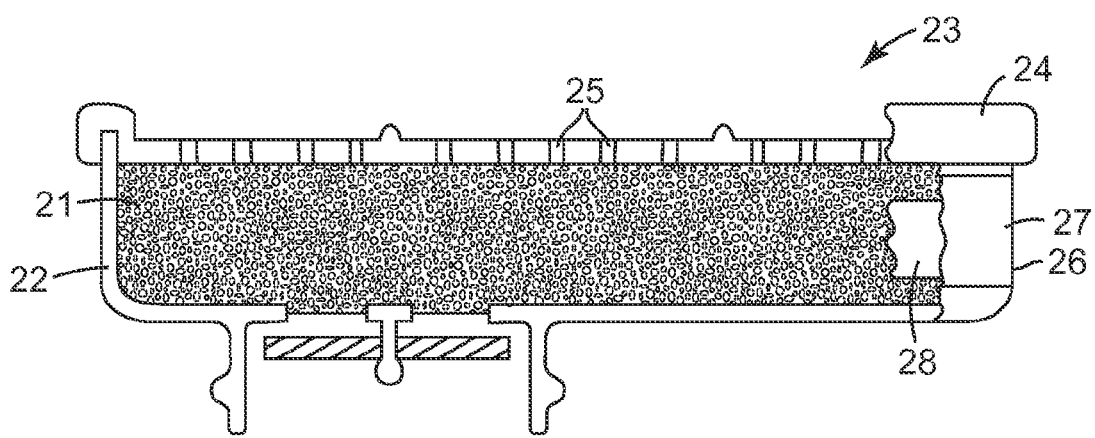
FIG. 16 shows a respirator cartridge suitable for use in exemplary embodiments of the present disclosure.

FIG. 16 is a side view, partially in section, of a respirator cartridge 23. If desired, the openings 25 could be sealed until use using for example a removable cover (not shown) that would be removed before use. A filter medium 21, such as bed of sorbent material, may absorb or adsorbs vapors of interest passing from the openings 25 to outlet 24. As is common in such devices, one-way inhalation valve may be mounted on a post prevents exhaled air from entering cartridge 23. A threaded or preferably bayoneted connector or connectors, such as those known to those of ordinary skill in the art, can be used to removably couple cartridge 23 to the face mask 20. As described in connection with FIGS. 1-3, the cartridge(s) 23 would be removed and replaced with fresh cartridge(s) when a change in at least one optical characteristic of the optical analyte sensor 28 indicates that the filter medium 21 underneath the optical analyte sensor 28 has become equilibrated with the analyte at the conditions of exposure. The change may be used to indicate the remaining service life for the cartridge 23, the end of its service life, or to give warning at the desired remaining service life percentage.

Figure 17A:
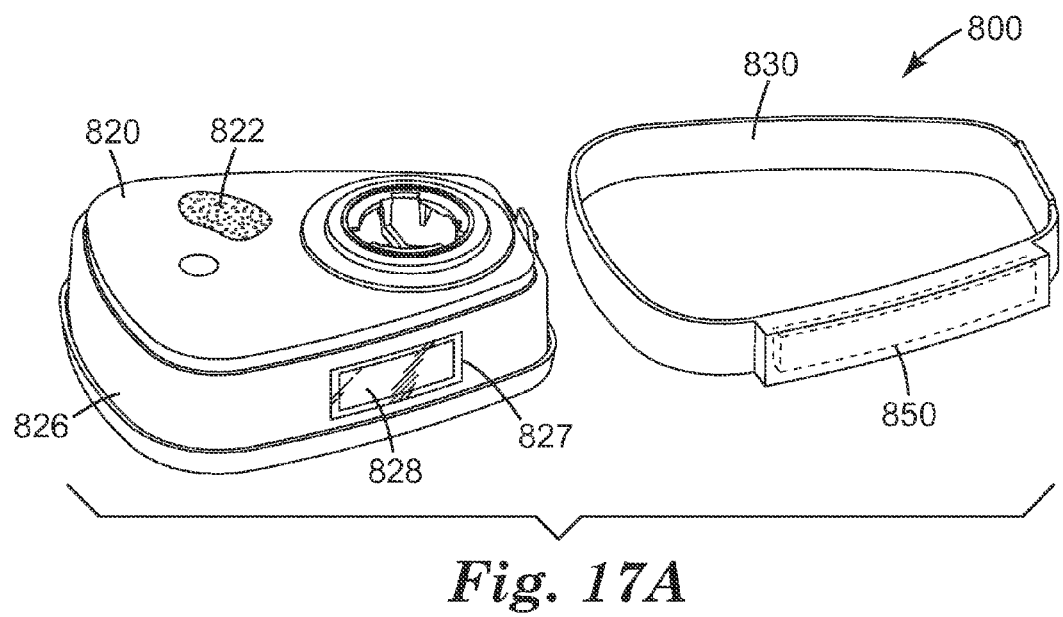
FIGS. 17A and 17B show yet another exemplary filter system according to the present disclosure.
Figure 17B:
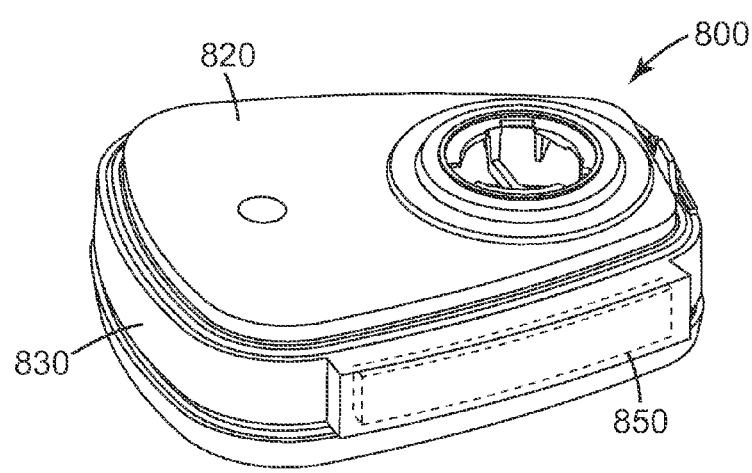

FIGS. 17A and 17B show another exemplary filter system 800 according to the present disclosure. In this exemplary embodiment, the exemplary filter system is a filter cartridge 800, which may be used in personal respirators, such as a personal respirator 2 described in connection with FIG. 15. The filter cartridge 800 includes a housing 820 and a filter medium 822, such as a sorbent material, e.g., activated carbon, disposed within the housing 820. An optical analyte sensor 828 is also disposed within the housing 820 in fluid communication with the filter medium 822. As explained above, the optical analyte sensor 828 may include a detection medium that changes at least one of its optical characteristics in response to an analyte, and it is disposed within the housing 820 such that the detection medium is in fluid communication with the filter medium 822. A wall 826 of a housing 820 may include a viewing port, such as a transparent portion 827 through which the optical analyte sensor 828 may be interrogated.

The filter system 800 further includes a removable housing portion 830 that is capable of being removably attached to the housing 820. The removable attachment of the removable housing portion 830 to the housing 820 may be effectuated by any suitable attachment mechanism, such as one or more one or more resilient snap-fit features, such as those shown in FIGS. 18A and 18B. Thus, in some exemplary embodiments, when the filter cartridge is expired, a removable housing portion can be readily removed and retained by the user for use on succeeding filter cartridges. Other suitable attachment mechanisms may include one or more latches, threaded features, such as a circumferential thread, a bayonet-style locking mechanism, separate engagement parts such as screws, nuts or clips engaging the housing 820 and the housing portion 830. In other exemplary embodiments, the housing portion 830 may be permanently attached, for example, by adhesive.

The filter system 800 includes an optical reader 850. The optical reader, including its circuitry and power source, can be permanently or removably attached to the housing portion 830. The housing portion 830, in turn, may be permanently or removably attached to the housing 820. As described above, the optical reader 850 may include at least one light source and at least one detector. The optical reader then should be attached to the removable housing portion 830 such that, when the removable housing portion 830 is attached to the housing 820, at least a portion of light emitted by at least one light source is reflected from the optical analyte sensor 828 and captured by at least one detector. The optical reader 850 may be disposed between the removable housing portion 830 and the optical analyte sensor 828, or some portions or components of the optical reader 850 may be disposed outside of the removable housing portion 830.

Figure 18A:
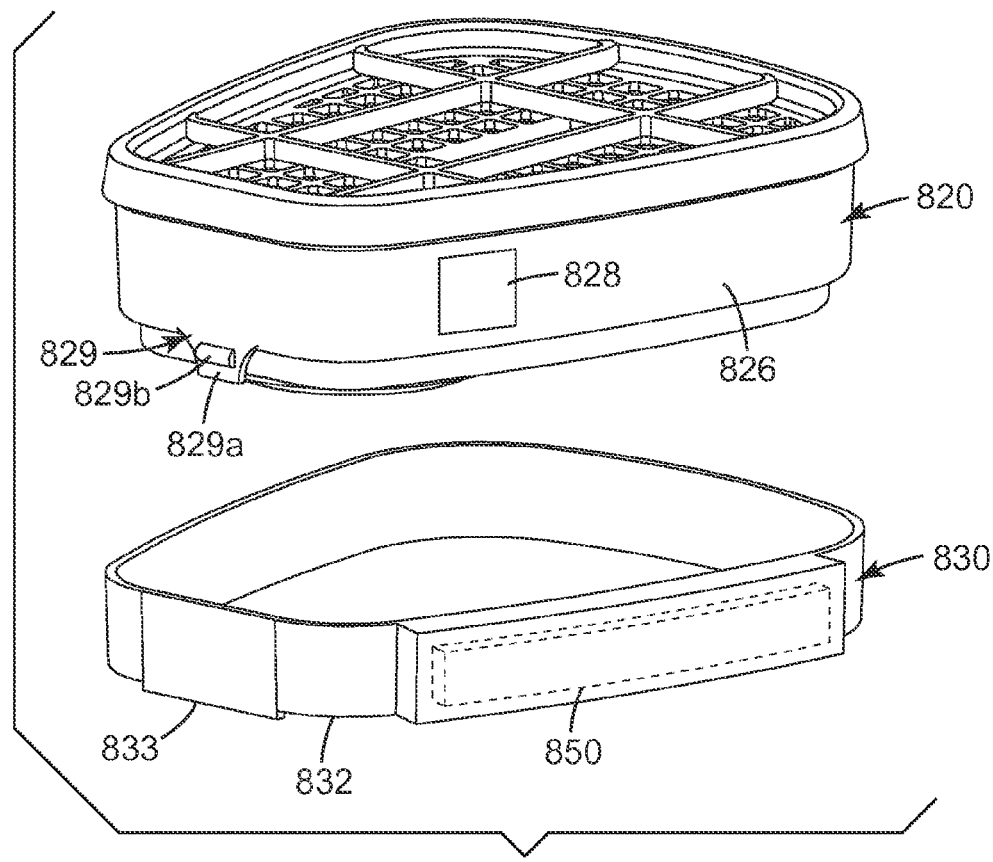
FIGS. 18A and 18B illustrate a suitable attachment mechanism that may be used in filter systems according to the present disclosure.
Figure 18B:
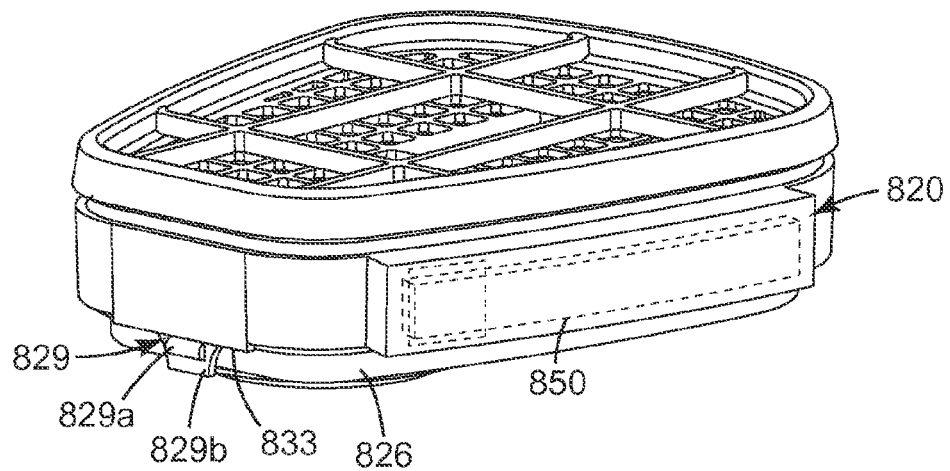

FIGS. 18A and 18B illustrate one suitable attachment mechanism that may be used, for example, in a filter system 800. FIG. 18A shows the removable housing portion 830 detached from the housing 820. In this exemplary embodiment, the side wall of the housing 826 has a latch structure 829 attached thereto. The latch structure 829 may include a projection 829a extending generally along the direction of the wall 826 and a retaining member 829b, projecting outwardly from the wall 826. The latch structure 829 is configured to engage a mating structure of the removable housing portion 830, such as a projection 833 of an edge 832 of the removable housing portion, as shown in FIG. 17B.

Although in FIGS. 16A-16B and 17A-17B, the removable housing portion 830 is shown as a structure encircling the outer wall 826 of the housing 820, the removable portion can take on a variety of other suitable shapes (see, e.g., FIG. 18). Although in some embodiments, the removable housing portion may be in the form of a collar or skirt, or a cover or cap, in other exemplary embodiments, the removable housing portion may cover only a portion of the outer wall of the housing.

Figure 19:
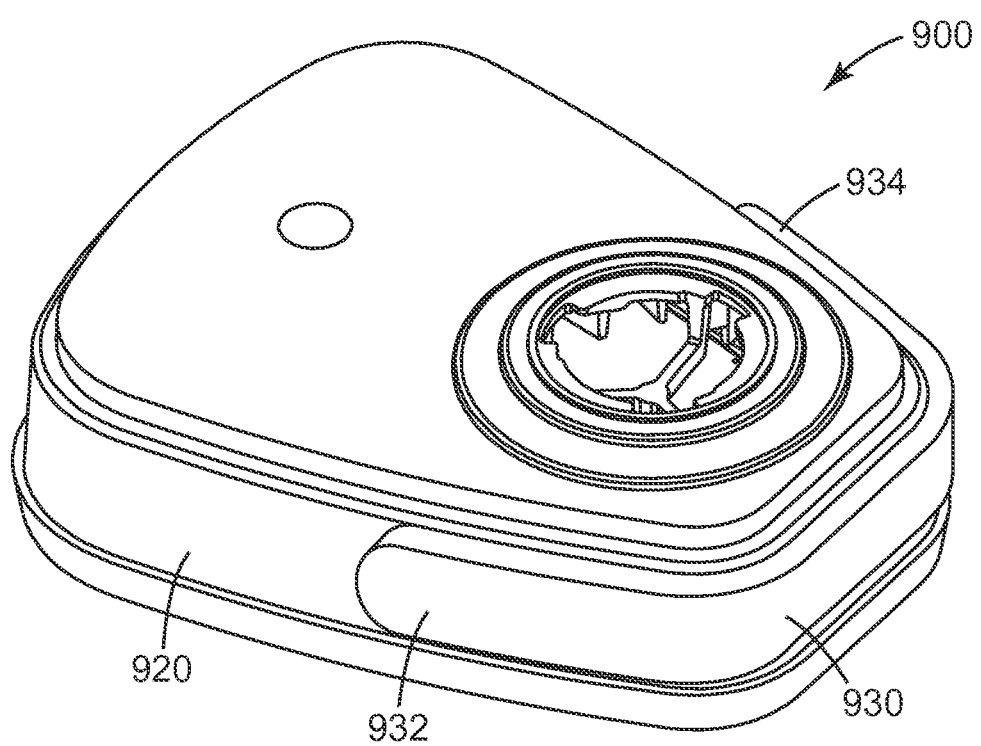
FIG. 19 shows another exemplary filter system according to the present disclosure.

Such a configuration is illustrated schematically in FIG. 19, which shows an exemplary filter system 900 according to the present disclosure. The filter system 900 includes a housing 920. The filter system 900 further includes a removable U-shaped housing portion 930 that is capable of being removably attached to the housing 920. The removable attachment of the removable housing portion 930 to the housing 920 may be effectuated by forming the removable housing portion 930 form a resilient material, such that the ends 932 and 934 of the removable housing portion operate as living hinges that each exerts a force on the housing 920 thus retaining the removable housing portion in place. Other suitable attachment mechanisms can also be used such as those described above in connection with other embodiments or any other suitable attachment mechanisms.

Exemplary embodiments including a removable housing portion (such as a collar or skirt) provide a convenient means of holding an optical reader in proximity to and in alignment with the optical analyte sensor that is included as a part of a respirator cartridge. In such exemplary embodiments, the optical reader can be detached as desired from the cartridge housing and/or from the removable housing portion and replaced into the assembly with highly reproducible positioning. The housing portion may also serve to mechanically protect the optical reader while in use. If constructed from opaque plastic and/or coated with a light-absorbing material, various parts of the filter assembly may prevents incoming light and thereby maintains consistent illumination for the optical reader.

It will be apparent to those skilled in the art that the specific exemplary structures, features, details, configurations, etc., that are disclosed herein can be substituted, modified and/or combined in numerous embodiments. For example, optical readers and/or optical analyte sensors described herein may be used with a variety of filter systems described herein or any other suitable filter systems. All such variations and combinations are contemplated by the inventors as being within the bounds of the conceived invention. Thus, the scope of the present invention should not be limited to the specific illustrative structures described herein, but rather by the structures described by the language of the claims, and the equivalents of those structures. To the extent that there is a conflict or discrepancy between this specification and the disclosure in any document incorporated by reference herein, this specification will control.

Examples

1. Optical Analyte Sensor Preparation

TABLE 2

Materials for PIMS Synthesis

| ABBREVIATION | DESCRIPTION |
| --- | --- |
| BC | bis-catechol; 5,5',6,6'-tetrahydroxy-3,3,3',3'-tetramethyl-1,1'-spirobisindane |
| FA | fluorinated arene; tetrafluoroterephthalonitrile |
| DMF | N,N-dimethylformamide |
| THF | tetrahydrofuran |

An optical analyte sensor of this example was a thin film indicator as depicted in FIG. 3A. It was prepared using a polymer of intrinsic microporosity (PIM) as the detection layer, a Ni partially reflective layer, and a silver nanoparticle vapor-permeable reflective layer. PIM polymer was prepared from the monomers BC and FA generally according to the procedure reported by Budd et al. in *Advanced Materials,* 2004, Vol. 16, No. 5, pp. 456-459. 9.0 grams of BC were combined with 5.28 g of FA, 18.0 g potassium carbonate, and 120 milliliters of DMF and the mixture was reacted at 70° C. for 24 hours. The resulting polymer was dissolved in THF, precipitated three times from methanol, and then dried under vacuum at room temperature (PIM Sample 50-2).

A metalized polyethylene terephthalate (PET) substrate was prepared by evaporatively depositing a 10 nm-thick Ni metal onto Melinex ST505 clear PET. The PIM polymer was dissolved at 4% concentration in chlorobenzene and solution deposited onto a base substrate consisting of Ni-coated PET.

Finally, a silver nanoparticle layer was deposited onto the PIM. 100 g of stock nanosilver solution (DGP-40LT-15C from Advanced Nanoproducts, Korea, 40 wt % silver) was diluted with 150 g of 1-methoxy-2-propanol and coated onto the PIM layer. After deposition, the overall sensor construction was heated at 130 Celsius for 12 hr to sinter the silver nanoparticles.

2. Filter Cartridge Preparation

A respirator cartridge was prepared by first adhering a 12 mm×25 mm piece of sensor film (described in Example 1) to the inner wall of a clear polycarbonate cartridge body using transfer adhesive (8172, 3M Company, St. Paul, Minn.). The cartridge body was then filled with 800 cc of Kuraray GC carbon (12×20 mesh size) and a retainer plate was ultrasonically welded to the body to contain the carbon and close the cartridge. The construction of the cartridge is shown in FIG. 2.

3. Optical Reader and Housing Preparation

To electronically interrogate the film sensor within the respirator cartridge, an optical reader containing two surface mount light emitting diodes (LED's) and a silicon photodetector was prepared. The detection optics i.e. LEDs and detector were mounted on the opposite sides of the printed circuit board with a cavity in the board. Light from the LEDs reflects off the film and irradiates the detector. This construction permits the reader to have a thin form factor and also prevents direct interference from the LEDs. The LED's were chosen with peak emission wavelengths of 591 nm and 606 nm. The reader functions by irradiating the sensor at these selected wavelengths in succession. The reflected light intensity is measured by the photodetector to determine the sensor response based on shifts in its visible reflectance spectrum.

A clear plastic housing was created using stereolithography (SLA) to house the optical reader. Clear resin from DSM Somos (Watershed 11120) was used to create the cassette. Such a reader is shown in FIG. 8.

4. Cartridge Skirt to House a Detachable Optical Reader

A plastic skirt for the respirator cartridge shown in FIG. 10D was created in black ABS resin. Shown in FIGS. 10A-10D are the skirt and its use in holding the detachable reader in proximity of the sensor. Although the skirt is depicted as detachably couplable to the filter cartridge, in this embodiment the skirt would likely be permanently attached to the filter with the reader detachably connected to the filter/skirt assembly. Used in this fashion, the skirt provides a robust means of attaching the reader and also protects the reader from mechanical abuse or from contamination (dust, mist, spray) within a working environment. The reader was attached to the skirt using a double sided adhesive tape.

5. Detachable Cartridge Skirt

This embodiment is similar to Example 4, but here the reader is permanently attached to the skirt, creating an assembly which can be removably coupled with the filter system. Use of a reader/skirt assembly minimizes chances of losing the reader during use, eliminates handling of the bare reader cartridge, and makes the overall system more robust.

6. Detachable Skirt or Sleeve for Cartridges That are Suitable for Reusable Negative Pressure Respirators This embodiment is similar to Example 5, but tailored to be used with the respirator cartridges for reusable negative pressure respirators. The reader is permanently attached to a skirt or sleeve which can be removably coupled with the cartridge. The user would remove and attach the reader/skirt assembly from the cartridge. This minimizes chances of losing the reader during use, eliminates handling of the bare reader cartridge, and makes the overall system more convenient to assemble and use. Such a device is expected to have the optical reader integrated into the collar and housed in a protective case with a see-through cavity to read the film on the cartridge.

What is claimed is:

1. A filter system comprising:
   a filter cartridge housing having a removable housing portion;
   a filter medium disposed within the filter cartridge housing;
   a optical analyte sensor comprising a detection medium that changes at least one of its optical characteristics in response to an analyte, the optical analyte sensor disposed within the filter cartridge housing and attached to a wall of the filter cartridge housing such that the detection medium is in fluid communication with the filter medium; and
   an optical reader comprising at least one light source and at least one detector, the optical reader attached to the removable housing portion such that, when the removable housing portion is attached to the filter cartridge housing, at least a portion of light emitted by at least one light source is reflected from the optical analyte sensor and captured by at least one detector,
      wherein the filter cartridge housing wall comprises a transparent portion to which the optical analyte sensor is attached and through which the optical analyte sensor is optically interrogatable by the optical reader,
      and wherein the filter cartridge housing wall to which the optical analyte sensor is attached is not a wall of the removable housing portion of the filter cartridge housing.

2. The filter system of claim 1, wherein the removable housing portion comprises a collar.

3. The filter system of claim 1, wherein the removable housing portion comprises a cover.

4. The filter system of claim 1, wherein the removable housing portion is removably attached to the housing by one or more resilient snap-fit features.

5. The filter system of claim 1, wherein the optical reader is disposed between the removable housing portion and the optical analyte sensor and wherein the removable housing portion comprises at least one opening disposed over optical reader.

6. The filter system of claim 5, wherein the optical reader comprises a visual indicator visible through the opening.

7. The filter system of claim 1, wherein the optical reader comprises an actuator.

8. The filter system of claim 1, wherein the optical reader is removably attached to the removable housing portion.

9. The filter system of claim 8, wherein at least one of the optical reader and the removable housing portion comprises at least one registration feature.

10. The filter system of claim 8, wherein the optical reader and the removable housing portion each comprise a registration feature.

11. The filter system of claim 10, wherein the optical reader comprises a slot and the removable housing portion comprises a rib.

\* \* \* \* \*

UNITED STATES PATENT AND TRADEMARK OFFICE
CERTIFICATE OF CORRECTION

PATENT NO.         : 8,821,621 B2                                       Page 1 of 1
APPLICATION NO.    : 13/634154
DATED              : September 2, 2014
INVENTOR(S)        : Gary Dwyer It is certified that error appears in the above-identified patent and that said Letters Patent is hereby corrected as shown below:

Title Page, Item (56),

Page 2, Column 1 (Other Publications)
Line 10, Delete "Antifeflection" and insert -- Antireflection --, therefor.

In the Specification

Column 1
Line 27 (Approx.), Delete "haz-mat" and insert -- hazmat --, therefor.

Column 10
Line 49, Delete "backing" and insert -- backing. --, therefor. (First Occurrence)

Column 13
Line 44, Delete "infra-read" and insert -- infrared --, therefor.

Signed and Sealed this
Tenth Day of February, 2015

Michelle K. Lee
*Deputy Director of the United States Patent and Trademark Office*